United States Patent
Alm et al.

(10) Patent No.: US 7,735,352 B2
(45) Date of Patent: *Jun. 15, 2010

(54) MULTI-DIMENSIONAL PORTABLE GAS CHROMATOGRAPH SYSTEM

(75) Inventors: Sheena Alm, Santa Barbara, CA (US); James Bentley, Salt Lake City, UT (US); John Blankevoort, Salt Lake City, UT (US); Mark Kaspersen, Goleta, CA (US); Collin Lewis, Wellsville, UT (US); Derek Maxwell, Sandy, UT (US); Ken Wunner, Riverton, UT (US)

(73) Assignee: Alliant Techsystems Inc., Minneapolis, MN (US)

( * ) Notice: Subject to any disclaimer, the term of this patent is extended or adjusted under 35 U.S.C. 154(b) by 695 days.

This patent is subject to a terminal disclaimer.

(21) Appl. No.: 11/435,375

(22) Filed: May 16, 2006

(65) Prior Publication Data
US 2007/0266858 A1    Nov. 22, 2007

(51) Int. Cl.
*G01N 30/66* (2006.01)
*B01D 53/02* (2006.01)

(52) U.S. Cl. .......... 73/23.4; 73/23.41; 73/23.42; 96/105; 96/106

(58) Field of Classification Search ........... 96/101, 96/102, 104, 105, 106; 95/82, 86, 87; 73/23.35, 73/23.36, 23.39, 23.4, 23.41, 23.42
See application file for complete search history.

(56) References Cited

U.S. PATENT DOCUMENTS

| | | | | |
|---|---|---|---|---|
| 2,057,150 A | * | 10/1936 | Kehl et al. | 137/505.12 |
| 2,813,010 A | | 11/1957 | Hutchins | 22/232 |
| 4,245,494 A | | 1/1981 | Legendre et al. | 73/23.1 |
| 4,293,316 A | | 10/1981 | Block | 55/16 |
| 4,474,889 A | | 10/1984 | Terry et al. | 436/161 |
| 4,726,822 A | * | 2/1988 | Cates et al. | 96/101 |
| 4,787,239 A | | 11/1988 | DiMatteo | 73/23.1 |
| 4,854,952 A | * | 8/1989 | Stepien | 96/105 |
| 4,883,504 A | | 11/1989 | Gerstel | 55/67 |
| 5,005,399 A | * | 4/1991 | Holtzclaw et al. | 73/23.39 |
| 5,049,509 A | * | 9/1991 | Szakasits et al. | 436/140 |
| 5,105,652 A | * | 4/1992 | Manfredi et al. | 73/23.25 |
| 5,108,466 A | | 4/1992 | Klein et al. | 55/20 |

(Continued)

OTHER PUBLICATIONS

Tenax TM -GR Adsorbent Resin for Trapping Volatiles, Dec. 17, 2004, Scientific Instrument Services, Inc., http://web.archive.org/web/20041217120833/www.sisweb.com/index/referenc/tenaxgrm.htm.*

(Continued)

*Primary Examiner*—Michael A Marcheschi
*Assistant Examiner*—Robert A Clemente
(74) *Attorney, Agent, or Firm*—Vidas, Arrett & Steinkraus, P.A.

(57) ABSTRACT

A portable multi-dimensional gas chromatograph, the gas chromatograph including a carrier gas container, a regulator fluidly connected to the carrier gas container, a dopant chamber containing a reference chemical, at least one pre-concentrator which is fluidly connected to the regulator and the dopant chamber, a first separation column fluidly connected to the at least one pre-concentrator, a second separation column fluidly connected to the at least one pre-concentrator, a first detector fluidly connected to the first separation column, and a second detector fluidly connected to the second separation column.

2 Claims, 44 Drawing Sheets

U.S. PATENT DOCUMENTS

| | | | | |
|---|---|---|---|---|
| 5,108,468 | A | 4/1992 | Ligon, Jr. | 55/67 |
| 5,135,549 | A | 8/1992 | Phillips et al. | 55/67 |
| 5,139,681 | A * | 8/1992 | Cortes et al. | 210/659 |
| 5,236,668 | A * | 8/1993 | Higdon | 422/89 |
| 5,298,225 | A * | 3/1994 | Higdon | 422/89 |
| 5,338,514 | A * | 8/1994 | Morabito et al. | 422/89 |
| 5,340,543 | A * | 8/1994 | Annino et al. | 422/89 |
| 5,525,799 | A | 6/1996 | Andresen et al. | 250/288 |
| 5,544,276 | A | 8/1996 | Loux et al. | 392/480 |
| 5,583,281 | A | 12/1996 | Yu | 73/23.42 |
| 5,611,846 | A | 3/1997 | Overton et al. | 96/102 |
| 5,612,225 | A | 3/1997 | Baccanti et al. | 436/114 |
| 5,634,961 | A * | 6/1997 | Gordon | 95/17 |
| 5,792,943 | A | 8/1998 | Craig | 73/61.52 |
| 5,804,701 | A * | 9/1998 | Berger | 73/23.42 |
| 5,808,179 | A | 9/1998 | Sittler et al. | 73/23.42 |
| 5,856,616 | A | 1/1999 | Maswadeh et al. | 73/23.42 |
| 5,928,459 | A * | 7/1999 | Geyer et al. | 156/331.1 |
| 5,939,614 | A * | 8/1999 | Walters et al. | 73/23.39 |
| 5,952,556 | A | 9/1999 | Shoji | 73/23.42 |
| 5,983,703 | A | 11/1999 | Wylie et al. | 73/23.42 |
| 6,006,780 | A | 12/1999 | Tseng et al. | 137/488 |
| 6,029,498 | A * | 2/2000 | Walters et al. | 73/23.39 |
| 6,029,499 | A | 2/2000 | Sittler et al. | 73/23.42 |
| 6,068,780 | A | 5/2000 | Yu | 216/10 |
| 6,093,921 | A * | 7/2000 | Gaisford et al. | 219/748 |
| 6,126,728 | A * | 10/2000 | Walsh et al. | 96/101 |
| 6,157,015 | A * | 12/2000 | Gaisford et al. | 219/748 |
| 6,165,251 | A * | 12/2000 | Lemieux et al. | 95/82 |
| 6,209,386 | B1 * | 4/2001 | Mustacich et al. | 73/23.39 |
| 6,217,829 | B1 * | 4/2001 | Mustacich et al. | 422/89 |
| 6,223,584 | B1 | 5/2001 | Mustacich et al. | 73/23.41 |
| 6,227,034 | B1 | 5/2001 | Trochesset | 73/23.42 |
| 6,306,200 | B1 | 10/2001 | Yu | 96/102 |
| 6,316,759 | B2 * | 11/2001 | Gaisford et al. | 219/748 |
| 6,351,983 | B1 | 3/2002 | Haas et al. | 73/23.37 |
| 6,374,860 | B2 | 4/2002 | Xu et al. | 137/884 |
| 6,454,527 | B2 | 9/2002 | Nishiyama et al. | 415/119 |
| 6,514,316 | B1 * | 2/2003 | Gaisford et al. | 95/87 |
| 6,524,527 | B2 | 2/2003 | Fimreite et al. | 420/648 |
| 6,575,015 | B2 | 6/2003 | Lechner-Fish et al. | 73/23.42 |
| 6,579,345 | B2 * | 6/2003 | Munari et al. | 95/87 |
| 6,601,606 | B2 | 8/2003 | Xu et al. | 137/341 |
| 6,607,580 | B1 | 8/2003 | Hastings et al. | 95/87 |
| 6,627,454 | B2 | 9/2003 | Amirav et al. | 436/161 |
| 6,632,268 | B2 * | 10/2003 | Seeley | 95/86 |
| 6,652,625 | B1 | 11/2003 | Tipler et al. | 95/82 |
| 6,682,699 | B2 * | 1/2004 | Mustacich et al. | 422/89 |
| 6,730,216 | B2 * | 5/2004 | Heringa et al. | 210/198.2 |
| 6,780,314 | B2 | 8/2004 | Jinno et al. | 210/198.2 |
| 6,814,785 | B2 | 11/2004 | Tipler et al. | 96/105 |
| 6,837,096 | B2 | 1/2005 | Stewart | 73/23.35 |
| 6,838,640 | B2 | 1/2005 | Wise et al. | 219/209 |
| 6,865,926 | B2 * | 3/2005 | O'Brien et al. | 73/23.27 |
| 6,928,858 | B2 * | 8/2005 | Lin | 73/25.03 |
| 6,948,520 | B2 | 9/2005 | Carroll | 137/505.25 |
| 6,952,945 | B2 | 10/2005 | O'Brien | 73/23.35 |
| 6,974,495 | B2 | 12/2005 | Tipler et al. | 96/105 |
| 7,130,534 | B1 * | 10/2006 | Miller, II | 392/416 |
| 7,137,286 | B2 * | 11/2006 | Furukawa | 73/23.42 |
| 7,228,067 | B2 * | 6/2007 | Magni et al. | 392/480 |
| 7,281,408 | B2 * | 10/2007 | Srinivasan et al. | 73/23.42 |
| 7,291,203 | B2 * | 11/2007 | Crnko et al. | 95/87 |
| 7,323,586 | B2 * | 1/2008 | Wiese et al. | 560/98 |
| 7,347,080 | B2 * | 3/2008 | Mahoney et al. | 73/23.4 |
| 7,361,208 | B2 * | 4/2008 | Botelho et al. | 95/87 |
| 2001/0000403 | A1 * | 4/2001 | Gaisford et al. | 219/748 |
| 2003/0037592 | A1 * | 2/2003 | D'Couto et al. | 73/23.35 |
| 2004/0144159 | A1 | 7/2004 | Stewart | 72/23.36 |
| 2004/0194628 | A1 | 10/2004 | Mitra | 96/101 |
| 2005/0106068 | A1 * | 5/2005 | Malik et al. | 422/89 |
| 2007/0084346 | A1 * | 4/2007 | Boyle et al. | 96/101 |
| 2007/0172960 | A1 * | 7/2007 | Malik et al. | 436/161 |

OTHER PUBLICATIONS

U.S. Appl. No. 11/435,382, filed May 16, 2006, Bently et al.
U.S. Appl. No. 11/435,366, filed May 16, 2006, Blankevoort et al.
U.S. Appl. No. 11/435,298, filed May 16, 2006, Bently et al.
Ebersold et al., "A Portable High Speed Gas Chromatograph for Field Monitoring," Photovac, Inc., pp. 1-5, (2003) http://www.environmental-expert.com/articles/atricle1291/article1291.htm.
http://www.chemistry.adelaide.edu.au/external/soc-rel/content/gc-det.htm, "Gas Chromatography (GC) Detectors," p. 1-2.
http://www.quadrexcorp.com/new/sri/sri.htm "Full-Featured Portable Gas Chromatographs From SRI Instruments" pp. 1-3.
"Portable Gas Chromatograph," PID Analyzers, LLC, http//www.hnu.com or www.processanalyzers.net, pp. 1-2.
Wahl et al., "A portable multi-dimensional gas chromatographic system for field applications," J. Sep. Sci., 26, pp. 1083-1090, (2003).
http://www.engineeringtalk.com/news/ail/ail03.html, "All-in portable gas chromatograph goes on-site," Agilent Technologies Europe, pp. 1-3, (2002).
http://www.quadrexcorp.com/new/sri/srispecs.htm "Model 8610 GC Mainframe Features," pp. 1-3, (2002).
http://news.thomasnet.com/fullstory/453257, "Portable Gas Chromatograph detects and measures VOCs," Archive News Story, pp. 1-5, (2004).
Posner, Judd C., "Portable Gas Chromatography," NIOSH Manual of Analytical Methods, pp. 75-81, (1998).

* cited by examiner

US 7,735,352 B2

MULTI-DIMENSIONAL PORTABLE GAS CHROMATOGRAPH SYSTEM

CROSS-REFERENCE TO RELATED U.S. APPLICATIONS

Not applicable.

STATEMENT REGARDING FEDERALLY SPONSORED RESEARCH

Not Applicable

FIELD OF THE INVENTION

The present invention relates to the field of identification of chemical compounds, and to apparatuses and methods for doing the same. More particularly, the present invention relates to the field of gas chromatography, and to apparatuses therefore.

BACKGROUND OF THE INVENTION

Gas chromatography (GC) is one of the valuable techniques of analytical chemistry for analysis of complex samples for both environmental and medical applications.

As a practical matter, a gas chromatograph is an analytical instrument that separates a gaseous sample, or a liquid sample which has been converted to a gaseous state, into individual compounds so that these individual compounds can be readily identified and quantified. A typical gas chromatograph includes an injector, an analytical separation column, a detector, and an output for displaying the results of the analysis.

The injector functions to convert samples to a gaseous state if needed, and moves the gaseous sample to the head of the analytical separation column in a narrow band. The separation column is typically a long coiled tube or the like, that separates the sample into its individual components. Separation columns typically contain liquid or solid materials as a stationary phase, and separate the individual components based on their affinity for the medium, i.e. polar compounds have an affinity for a polar medium and non-polar compounds have an affinity for a non-polar medium, and their molecular weights as they are swept through the column with a carrier gas. Typically, the larger the molecule, the longer it is immobilized within the solid or liquid material within the column, and the longer it is retained within the column.

The detector then detects and measures the constituent components as they emerge from the analytical column. Different sample components are retained for different lengths of time within the column, and arrive at the detector at characteristic times. These "retention times" are used to identify the particular sample components, and are a function of the type and amount of sorbtive material in the column, the column length and diameter, the carrier gas type and flow rate, and of the column temperature. Temperature control is a factor in obtaining repeatable data.

The output displays the results of the analysis to the user.

Gas chromatography is one of the most widely used and accurate methods for chemical identification. However, typical gas chromatographs which are employed in the laboratory are dimensionally large, heavy and not easily transported for use in the field.

In recent years, the interest in having portable, lightweight gas chromatographs capable of accurately detecting low and mid-levels of chemical agents has increased significantly. For example, there is a high interest in the use of such detectors to detect chemicals which may be used in warfare or for terroristic activities.

There remains a need in the art for an improved, lightweight, portable gas chromatograph which can accurately detect and transmit to a user, low to mid-level concentrations of chemical and/or biological agents.

In some embodiments, a gas chromatograph may use a thermal conductivity detector to detect and measure the constituent components of the gasses being analyzed. Thermal conductivity detectors utilizing thermistors are generally known in the art. Such thermistors are generally extremely small and fragile, and therefore the use of thermal conductivity detectors has typically been limited to fixed instruments that are kept in a very stable laboratory environment. There remains a need for a rugged thermal conductivity detector capable of withstanding the vibrations and temperature variations associated with use in the field.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The present invention relates to portable, multi-dimensional gas chromatographs (GCs).

In one embodiment, the present invention relates to portable, multi-dimensional gas chromatographs having at least two separation columns, at least one detector for each of said at least two separation columns, at least one pre-concentrator; and at least one reference chemical.

In one embodiment, at least one of the two separation columns is part of a gas chromatograph column assembly (GCCA), the GCCA including a first housing, the first housing defining a first chamber. The GCCA further including a column support, wherein the column support is ring-shaped about an axis and includes a circumferential outer surface oriented about the axis and a plurality of axially oriented bridges, the bridges extending radially from the outer surface of the column support, and wherein the column support is positioned within the first chamber. Column tubing is then wound around the column support, wherein the column tubing is in contact with the plurality of bridges and is separated from the outer surface of the column support. Suitably, the GC includes at least two GCCAs, each GCCA including a separation column.

Each detector may be selected from any of a variety of suitable detectors. In one embodiment, at least one of the detectors is a thermal conductivity detector (TCD) having high sensitivity and capability of measuring chemical compounds at very minute concentrations, and suitably at least two of the detectors are TCDs.

In one embodiment, at least one of the separation columns includes a stationary phase which is polydimethylsiloxane.

In one embodiment, at least one of the separation columns includes a stationary phase which is polyethylene glycol.

In one embodiment, the pre-concentrator includes a graphitized carbon-based molecular sieve.

In one embodiment, the reference chemical is 1,4-dichlorobenzene.

The GC according to the invention, in various embodiments further includes a gas flow regulator for providing gas to the system at a consistent gas flow rate regardless of the pressure at which the gas is supplied.

At least one embodiment of the inventive gas regulator is directed towards a two stage gas regulator. The gas regulator has a gas flow path which receives gas from a gas source and outputs it at a reduced pressure. Each stage uses a piston assembly to reduce the pressure of the gas from an entering pressure to an exiting pressure. The gas flow path as a whole has three pressure levels, an input pressure, an intermediate pressure, and an output pressure. The input pressure is caused by the gas source (usually thousands of psi) which enters the first stage. The intermediate pressure (usually hundreds of psi) then exits the first stage and enters the second stage. The output pressure equal to the desired level (usually tens of psi) exits the second stage. The stages are oriented parallel to each other with their respective inputs and outputs facing in opposite directions. Diagnostic devices and manual shutoff assemblies further assist in operating the regulator. The regulator is compact and can be assembled out of common commercially available part.

The GC according to the invention in various embodiments includes at least one flow controller.

The GC according to the invention in various embodiments further includes at least one multiport valve having first and second positions for loading, analyzing and cleaning of the unit.

The GC according to the invention further includes a signal processing unit (SPU) in communication with the detectors. In various embodiments, the SPU further includes analog processing electronics in communication with the detectors which are further in communication with digital processing equipment.

The SPU further includes a CPU having a recognition library.

In at least one embodiment, a thermal conductivity detector comprises a housing having an internal gas analysis chamber, a fluid inlet passageway in communication with the gas analysis chamber, a fluid outlet passageway in communication with the gas analysis chamber, and a first bore extending through at least a portion of the housing. The first bore is in fluid communication with the gas analysis chamber, and is offset from the fluid inlet and outlet passageways. The thermal conductivity detector further comprises a thermisor having an electrical lead and a first contact pin electrically connected to the electrical lead. The first contact pin is oriented within the first bore, is electrically insulated from the housing and mechanically secured to the housing.

These and other aspects, embodiments and advantages of the present invention will become immediately apparent to those of ordinary skill in the art upon review of the Detailed Description and Claims to follow.

BRIEF DESCRIPTION OF THE DRAWINGS

FIG. 9A shows more detailed circuit schematics for the block diagram of FIG. 9.

FIG. 10A-1 through 10A-29 are more detailed circuit schematics of the various blocks of digital board, of FIG. 10.

FIG. 11B and FIG. 11C are more detailed circuit schematics showing how the detectors are connected to the FPGA peripheral controller/data formatter.

FIG. 12 shows a system firmware context diagram.

FIG. 13 is a gas chromatograph with interior parts visible.

FIG. 14 is a perspective view of an embodiment of a Gas Chromatograph Column Assembly (GCCA).

FIG. 15 is a perspective view of an embodiment of a GCCA.

FIG. 16 is a perspective view of an embodiment of a GCCA with a portion being transparent.

FIG. 17 is a blow-up view of an embodiment of a GCCA.

FIG. 18 is a blow-up view of an embodiment of a GCCA.

FIG. 19 is a side vies of an embodiment of a column support.

FIG. 20 is cross-sectional view along lines 19A-19A of FIG. 19.

FIG. 21 is a partial cross-sectional view along lines 19A-19A of FIG. 19.

FIG. 22 is a partial cross-sectional view along lines 19B-19B of FIG. 19.

FIG. 23 is a partial cut-away perspective view of an embodiment of a GCCA.

FIG. 24 is a partial cut-away perspective view of an embodiment of a GCCA.

FIG. 25 is a partial cut-away side view of an embodiment of a GCCA.

FIG. 26 is a cross-sectional perspective view of an embodiment of a capillary column.

FIG. 27 shows an exploded view of an embodiment of a thermal conductivity detector.

FIG. 28 shows an embodiment of a sensor housing portion of a thermal conductivity detector.

FIG. 29 shows embodiments of a body housing and a sensor housing for a thermal conductivity detector.

DETAILED DESCRIPTION OF THE INVENTION

Figure 1:
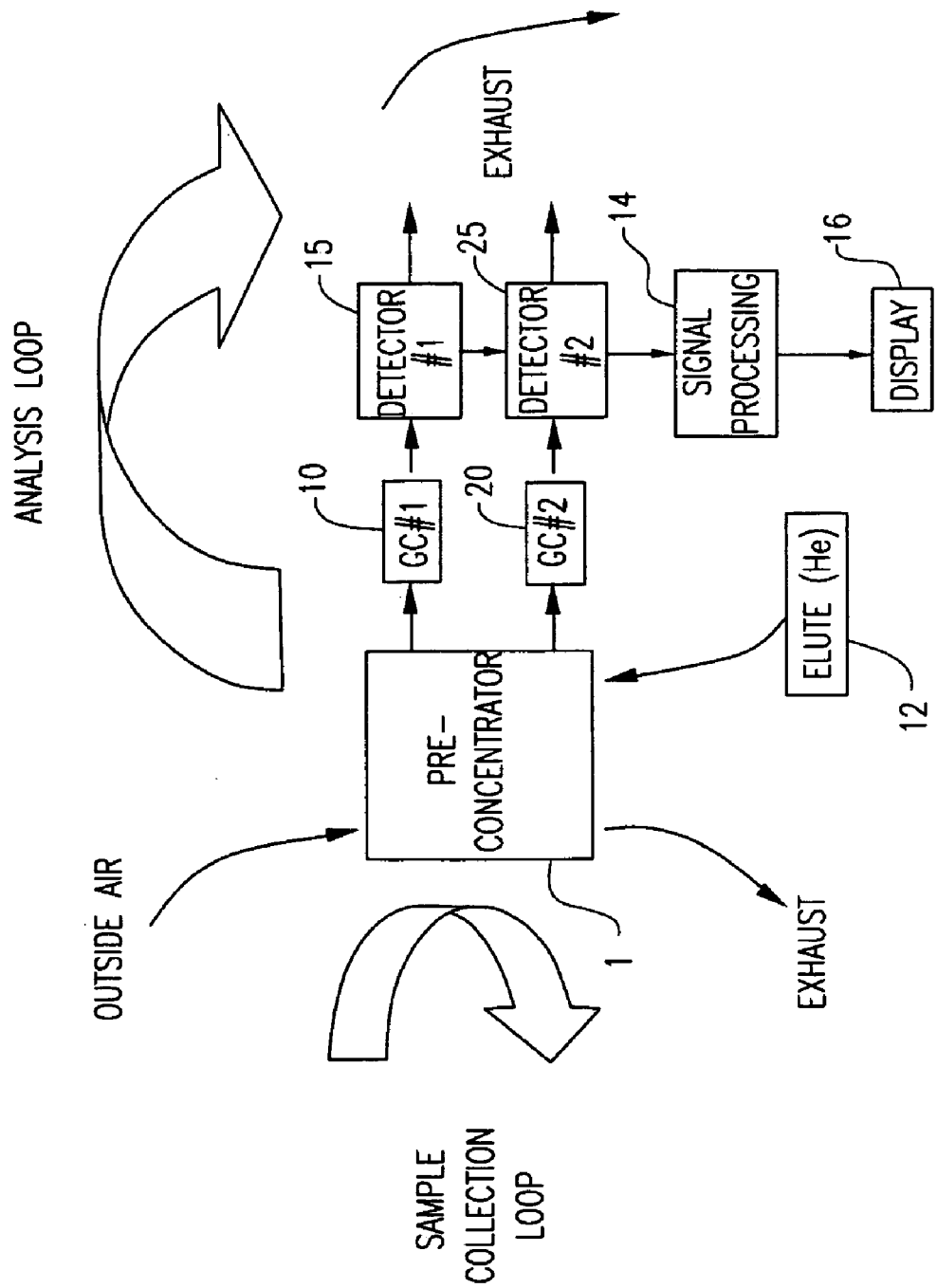
FIG. 1 is a simple block flow diagram of an embodiment of the gas chromatograph according to the invention.

While this invention may be embodied in many forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In a broad aspect, the present invention is directed to a portable gas chromatograph. Suitably, the chromatograph being portable, is between about 15 and 25 pounds.

The portable gas chromatograph includes at least one pre-concentrator, a first separation column, a second separation column, a first detector in communication with the first separation column and a second detector in communication with the second separation column.

In one embodiment, the detectors further have output signals which are connected to a signal processing unit. In specific embodiments, the signal processing unit includes, among other features, analog processing electronics, digital processing electronics in communication with the analog processing electronics, a central processing unit, and a recognition library.

In another embodiment, the signal processing unit is equipped with a wireless radio that may communicate with a computer within a given range of operation.

Turning now to the figures, FIG. 1 is a block flow diagram illustrating an embodiment of the gas chromatograph system according to the invention. Air is extracted from the surrounding environment into the pre-concentrator (1) using any suitable method known in the art such as via means of an air pump. Inside the pre-concentrator (1), the desired analytes are pre-concentrated to remove moisture to facilitate an increase in the size of the chromatographic peak achieved. Therefore, absorbents or adsorbent traps such as molecular sieves are employed. One example of a suitable adsorbent trap is graphitized carbon-based molecular sieve available from Alltech Associates Inc. (Alltech Associates, Inc., is a wholly owned subsidiary of W. R. Grace & Co. in Columbia, Md.) under the tradename of Tenex®.

The pre-concentrator may also be referred to as a thermal desorption tube.

Various methods have been suggested to pre-concentrate analytes. For example, see U.S. Pat. Nos. 2,813,010, 4,245, 494, 4,293,316, 5,612,225, 6,223,584, 6,652,625, 6,814,785, 6,977,495, each of which is incorporated by reference herein in its entirety.

The pre-concentrator (1) is also suitably equipped with a heater and heater electronics. Upon heating, the analyte is released into a carrier gas stream. In this embodiment, the carrier gas is helium. However, other suitable carrier gases include hydrogen and nitrogen, for example. Heating of the pre-concentrator is desirable because higher sample equilibrium temperatures can result in much larger chromatographic peaks.

From the pre-concentrator (1), the analyte in the carrier gas is then flowed substantially simultaneously into a first separation column (10) and a second separation column (20). The separation column(s) of the GC system contains the stationary phase through which the carrier gas with the analytes is flowed. The separation columns may contain any of a variety of suitable stationary phases.

1) Suitably, the stationary phase is formed using with a polymer material. Examples of suitable stationary phases include, but are not limited to, polydimethylsiloxane, polyethylene glycol and polyester polymers. Typically, the stationary phase is of a relatively high molecular weight.

Suitably, in the embodiment illustrated in FIG. 1, one of the columns 10, 20 includes a non-polar stationary phase, and one of the columns 10, 20 includes a polar stationary phase.

The nonpolar end of the spectrum is polydimethyl siloxane, which can be made more polar by increasing the percentage of phenyl groups on the polymer. For very polar analytes, polyethylene glycol (a.k.a. carbowax) is commonly used as the stationary phase. In the embodiment described above, for example, one column includes a stationary phase which is polydimethylsiloxane, a relatively non-polar molecule, and one column includes polyethylene glycol, a relatively polar molecule. After the polymer coats the column wall or packing material, it is often cross-linked to increase the thermal stability of the stationary phase and prevent it from gradually bleeding out of the column.

Suitably, the separation columns have a length of about 15 meters or longer. However, the separation columns are fitted into a small, compact portable unit as disclosed herein. As such, the separation columns are suitably configured into a gas chromatograph column assembly (GCCA). One suitable configuration for the separation columns disclosed herein is found in commonly assigned copending U.S. patent application Ser. No. 11/435,382 entitled Gas Chromatograph Column Assembly GCCA, the entire content of which is incorporated by reference herein. The GCCA is discussed in more detail with reference to FIGS. 14-26 found below.

In the embodiment shown in FIG. 1, first column 10 is in fluid communication with a first detector 15 and second column 20 is in fluid communication with a second detector 25.

Any suitable detector may be employed herein. Examples of suitable detectors include, but are not limited to, atomic emission, chemiluminescence, electron-capture (ECD), flame ionization (FID), photoionization (PID), mass spectrometer (MS), thermal conductivity (TCD), flame photometric (FPD), infrared (IFD), Fourier Transform infrared (FTIR), ultraviolet/visible, far ultraviolet absorbence (FUV) and nitrogen phosphorous (NPD). Detectors suitable for use in combination with gas chromatograph systems are disclosed in U.S. Pat. Nos. 6,952,945, 6,837,096, 6,627,454, 6,524,527 and 5,108,466, each of which is incorporated by reference herein in its entirety.

An example of a particular TCD type detector suitable for use herein is disclosed in commonly assigned copending patent application Ser. No. 11/435,298, entitled Compact Thermal Conductivity Detector, the entire content of which is incorporated by reference herein. An example of a specific TCD detector employed in combination with a GC according to the invention is discussed in more detail with reference to FIGS. 27-32.

Suitable detectors 15, 25 have the sensitivity to measure chemicals at a concentration of parts per one hundred million to parts per billion.

From detectors 15, 25, the gas with the analytes, is exhausted back into the environment.

Detectors 15, 25 measure each analyte and provide a signal to the signal processing unit. The signal processing unit is discussed in more detail with reference to FIG. 9 below. The signal processing unit includes analog signal processing electronics, digital signal processing electronics, and a central processing unit (CPU) The CPU records the signature of the chemical. A recognition library is also suitably incorporated into the CPU. The signature of the chemical is then compared to those in the recognition library and the chemical can be identified. The CPU then sends the data to a display 16.

Figure 2:
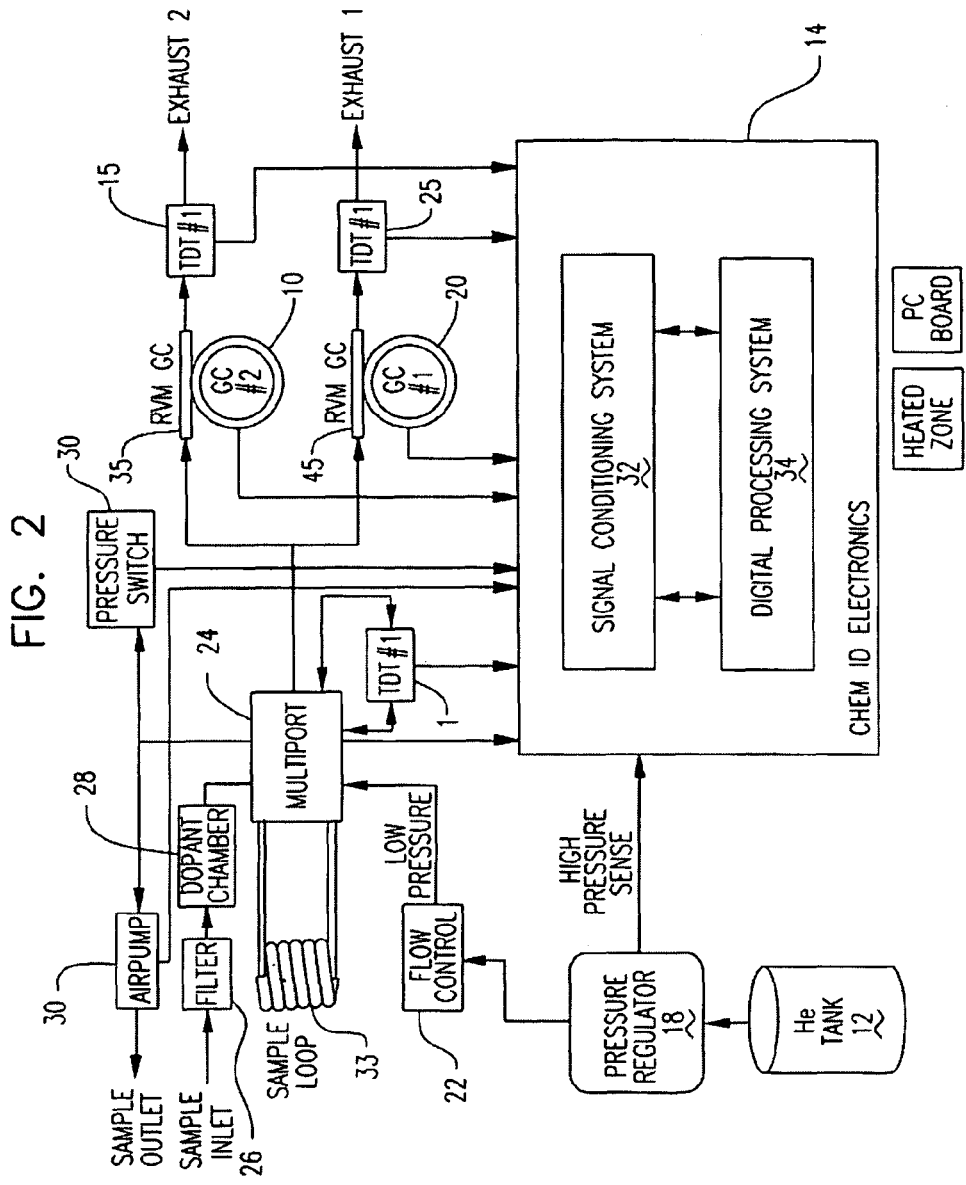
FIG. 2 is an enhanced block flow diagram of an embodiment of the gas chromatograph according to the invention.

FIG. 2 is an enhanced block flow diagram of a GC according to the invention. A carrier gas supply 12 is coupled with a pressure regulator 18 for controlling/reducing the pressure of the gas and a flow controller 22 for further maintaining gas flow rate to the GC columns 15, 25. The pressure regulator is selected from any suitable configuration. A specific example of a pressure regulator employed in combination with the GC according to the invention is disclosed in commonly assigned copending Ser. No. 11/435,366 entitled Very Small High Pressure Regulator, the entire content of which is incorporated by reference herein in its entirety.

The gas pressure of the carrier gas is regulated so that the sample flow of gas through the system can be controlled to a consistent flow whether the carrier gas in the tank is at a pressure of 2000 psi or 300 psi.

An embodiment of a specific gas pressure regulator employed herein is discussed in more detail below with reference to FIGS. 33-42.

The flow controller allows the gas flow to be selectively set and maintained.

The carrier gas is selected from any suitable inert gas including, but not limited to, hydrogen, helium and nitrogen. In the embodiment shown in FIG. 2, helium is shown as the carrier gas.

In the embodiment shown in FIG. 2, from the carrier gas supply 12, the gas is delivered via the flow controller 22 to a multiport valve 24 having switchable arrangement to allow for switching between operating states which will be explained more fully below. In a first operating state, however, sample is extracted from the surrounding environment through filter 26

A sample is extracted from the environmental surroundings through a filter 26. The sample is then passed through a dopant chamber 28 where it is mixed with reference chemical. A reference chemical is employed for removing errors caused by variations in temperature and/or pressure. As will be explained more fully below, the reference chemical has a known signature and any required correction for error based on the known signature is accomplished via signal processing software which provides a correction factor that will be applied against the other analytes in the sample being analyzed. A reference chemical is therefore included as part of each sample analysis.

The sample and the reference chemical are moved via the multiport valve 24 to the pre-concentrator 1, and from there directed to GC columns 10, 20. GC columns 10, 20 are in fluid communication with detectors 15, 25. Each detector 15, 25 is has its own output signal and each detector is in communication with a signal processing unit 14, which in FIG. 2 is shown broken down into a signal conditioning system 32 and a digital processing system 34.

As shown in FIG. 2, each GC column 10, 20, is equipped with its own heater 35, 45 respectively, each heater having its own heater electronics. This allows heating of each column 10, 20 to be heated from ambient temperatures to over 200° C. uniformly across the column length. It is also desirable that each column can be cooled between samples to ambient temperature within several minutes to allow for repeated sample measurements in short time periods.

Figure 3:
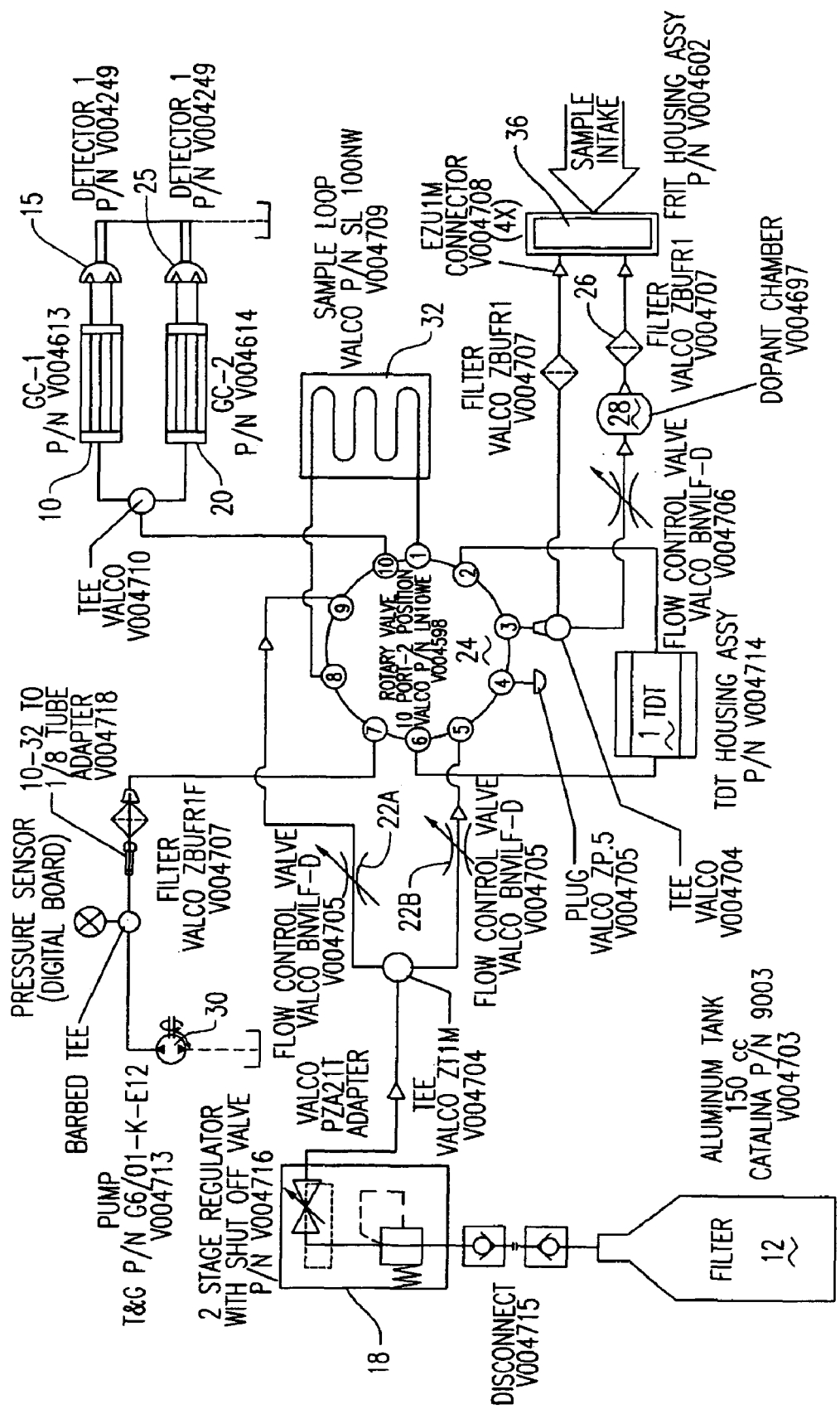
FIG. 3 is a pneumatic block diagram of an embodiment of the gas chromatograph according to the invention.

FIG. 3 is a pneumatic block flow diagram of the GC according to the invention which is a more detailed flow diagram of an embodiment similar to that shown in FIG. 2. In the embodiment shown in FIG. 3, the multiport valve 24 is shown as a 10-port valve having two positions, position A and position B.

Figure 4:
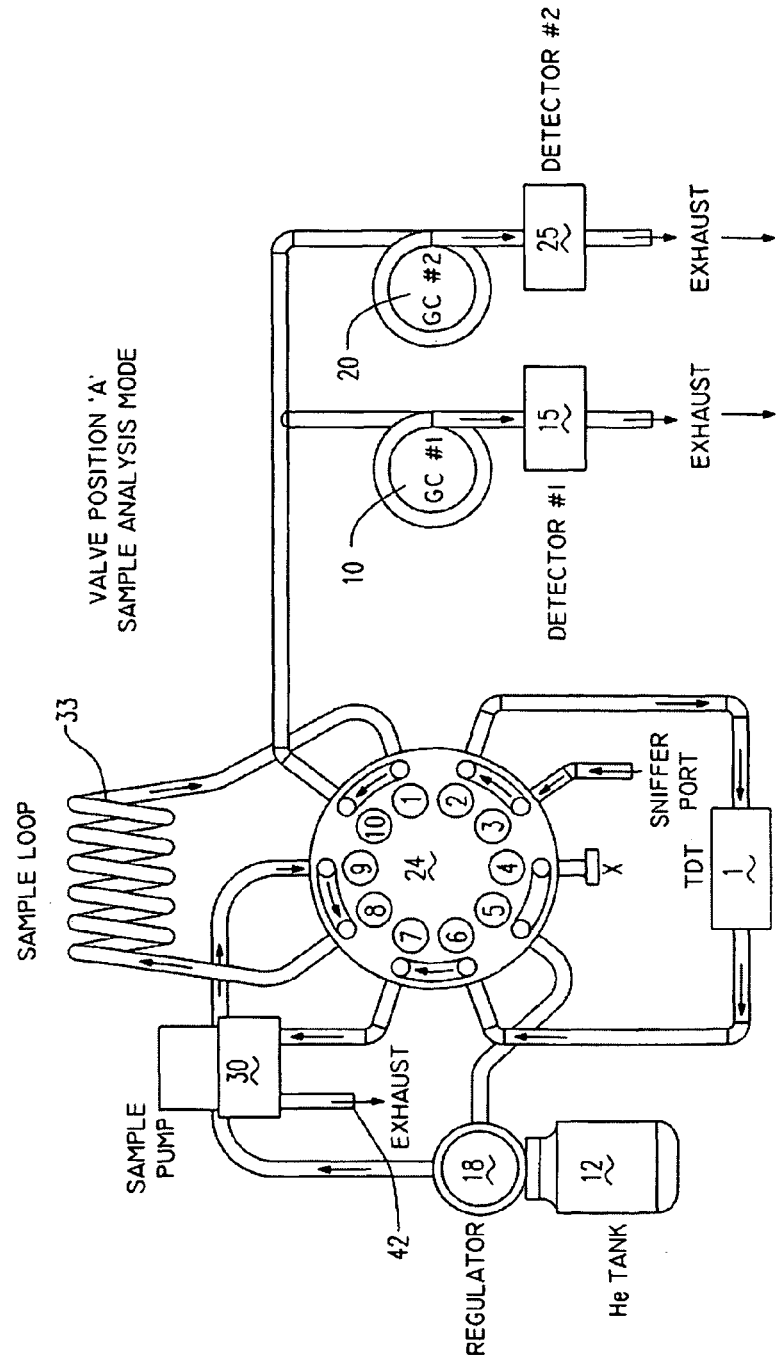
FIG. 4 is a schematic diagram of an embodiment of a multiport valve in combination with a gas chromatograph according to the invention shown in a first position.

In position A, a sample can be loaded. FIG. 4 is a schematic diagram of a multiport valve system 24 employed in the embodiment in FIGS. 2 and 3 shown in position A. A carrier gas, in this case helium, is provided from helium supply tank 12 (through valves as shown in FIG. 3) through regulator 18 through sample loop 33 through columns 10, 20 and detectors 15, 25 out exhaust ports 38, 40. When columns 10, 20 and detectors 15, 25 are on and being heated, carrier gas, i.e. in this embodiment helium, will be flowing through them. From a cold start-up, helium will flow until the unit reaches its predetermined operating temperature.

Once analysis is begun, typically by an operator activating a start button, in this embodiment the sample pump 30 is activated and a sample will be drawn through an inlet port designated at 36 (through valves as shown in FIG. 3) and to the pre-concentrator 1. From the pre-concentrator 1 the sample flows (through valves as shown in FIG. 3) through the sample pump and out exhaust port 42.

Figure 5:
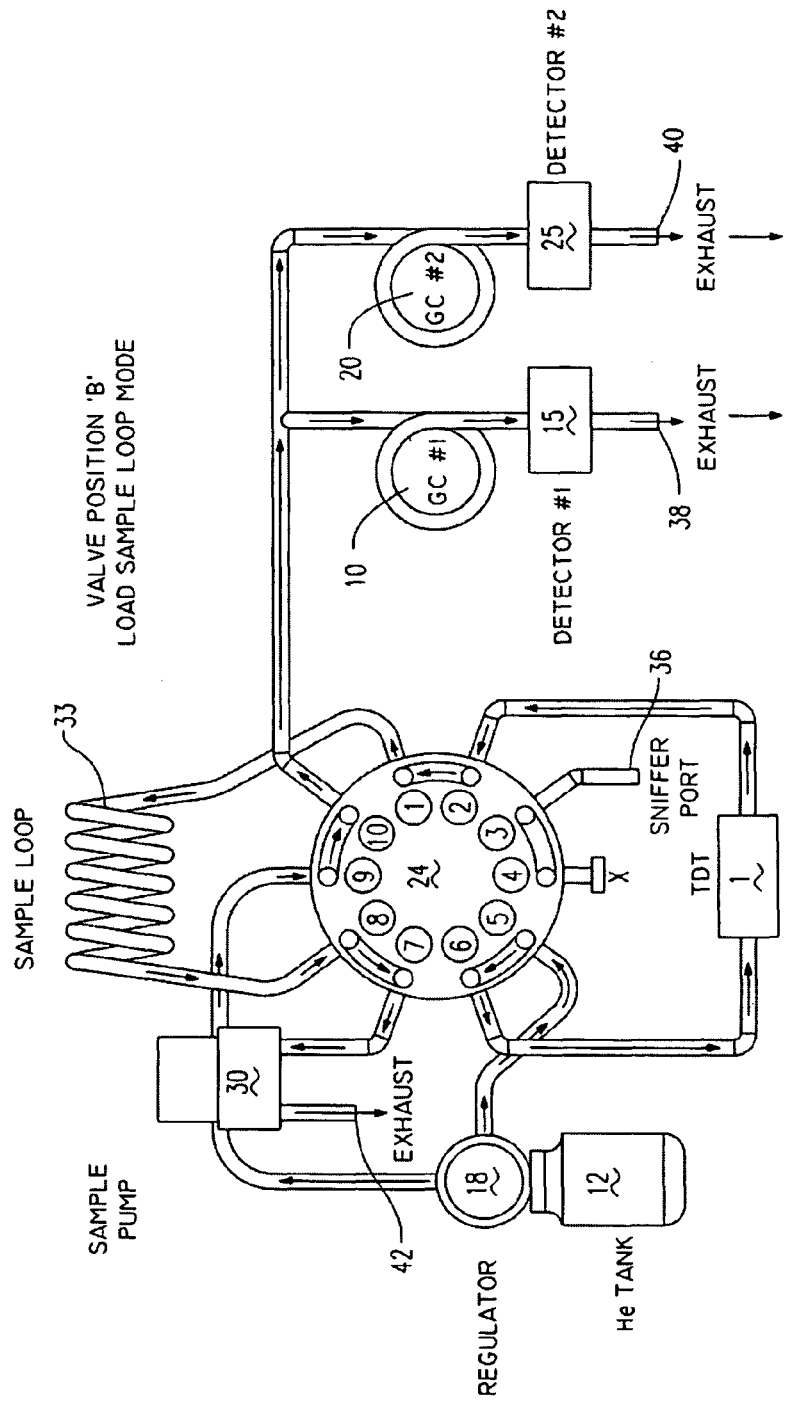
FIG. 5 is a schematic diagram of an embodiment of a multiport valve in combination with a gas chromatograph according to the invention shown in a second position.

A sample can be advanced to the GC columns 10, 20 when the multiport valve is advanced to position B. The multiport valve 24 is then switched to position B which is shown as a schematic diagram in FIG. 5. The pre-concentrator 1 is then heated (pre-concentrator is equipped with a heater and heater electronics as discussed above) which releases a cloud of the now concentrated sample. Helium flows from the regulator 18 (through valves 22A, 22B as shown in FIG. 3) through the pre-concentrator 1 (through valves as shown in FIG. 3) through the sample loop 32 (through valves as shown in FIG. 3) and out the exhaust port 42. Once the sample is caught in the sample loop, the multiport valve is switched back to position A. This only takes a short period of time. The sample loop 33 provides an internal volume for temporary storage of the concentrated sample provided from the pre-concentrator 1.

The sample can then be analyzed once the multiport valve 24 is again returned to position A. Again in position A, helium flows from carrier gas supply 12 (through valves 22A, 22B as shown in FIG. 3) through the sample loop 33 (through valves as shown in FIG. 3) and through the GC columns 10, 20 and to the detectors 15, 25. The carrier gas flowing through the system carries the now concentrated sample from the sample loop 33 to the GC columns 10, 20 and to the detectors 15, 25 for analysis. The multiport valve 24 can then be returned to position B for cleaning.

Once analysis is complete, multiport valve 24 is again switched to position B where helium continues to flow from the carrier gas supply 12 for clearing sample from the preconcentrator 1 and the sample loop 33.

Figure 6:
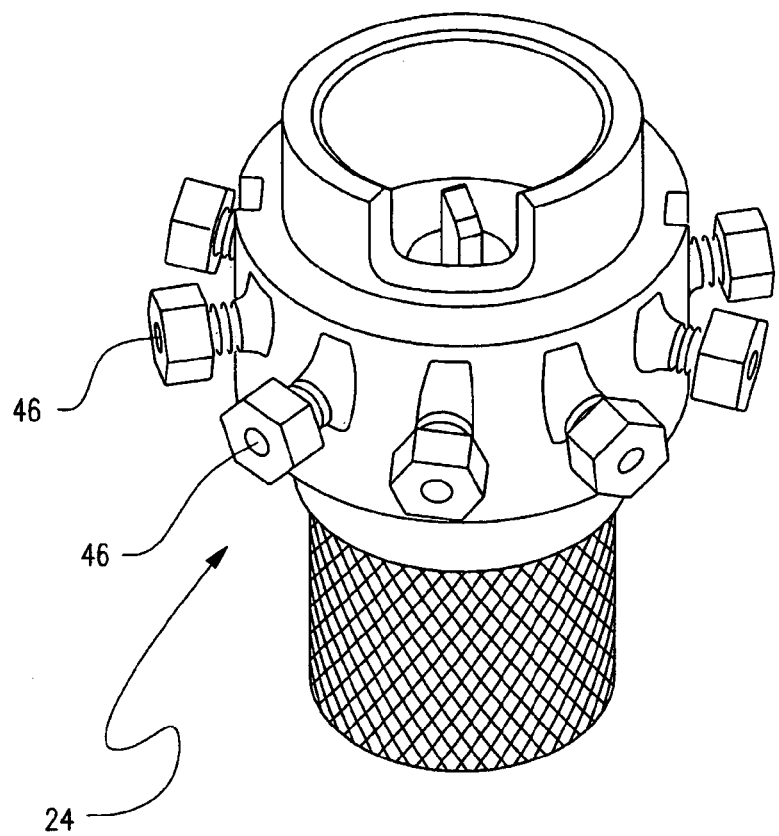
FIG. 6 illustrates a specific embodiment of a multiport valve.

FIG. 6 illustrates one embodiment of a multiport valve 24 employed in the GC according to the invention. The multiport valve 24 in this embodiment is shown having ten ports 46.

Figure 7:
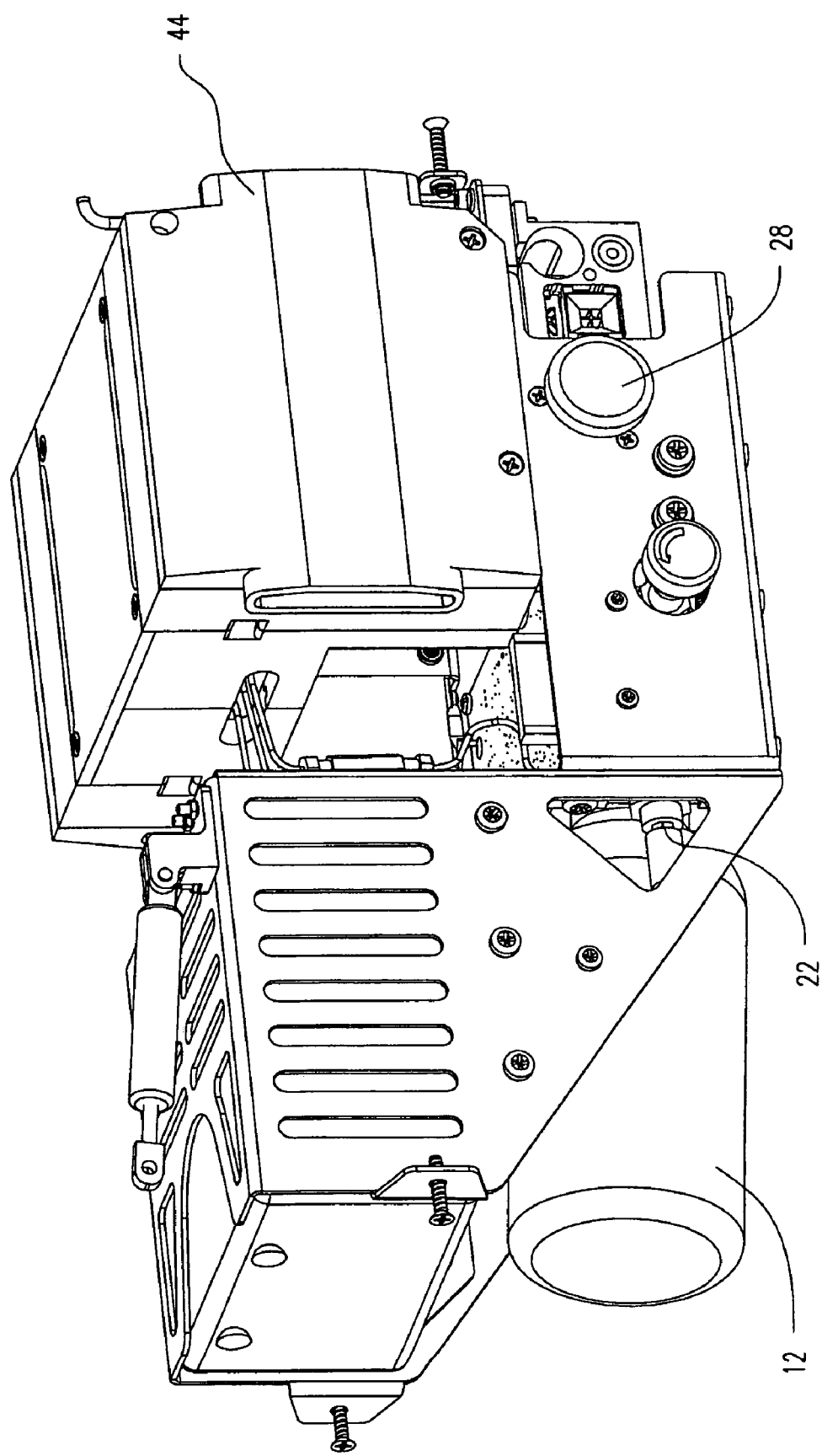
FIG. 7 is a side schematic of an embodiment of a compact gas chromatograph according to the invention.

FIG. 7 is a side view of an embodiment of a gas chromatograph 5 according to the invention. The GC columns 10, 20 and multiport valve 24 are held within casing 44. The carrier gas supply 12, flow control valve 22 and chamber 28 for the reference chemical are clearly seen.

Figure 8:
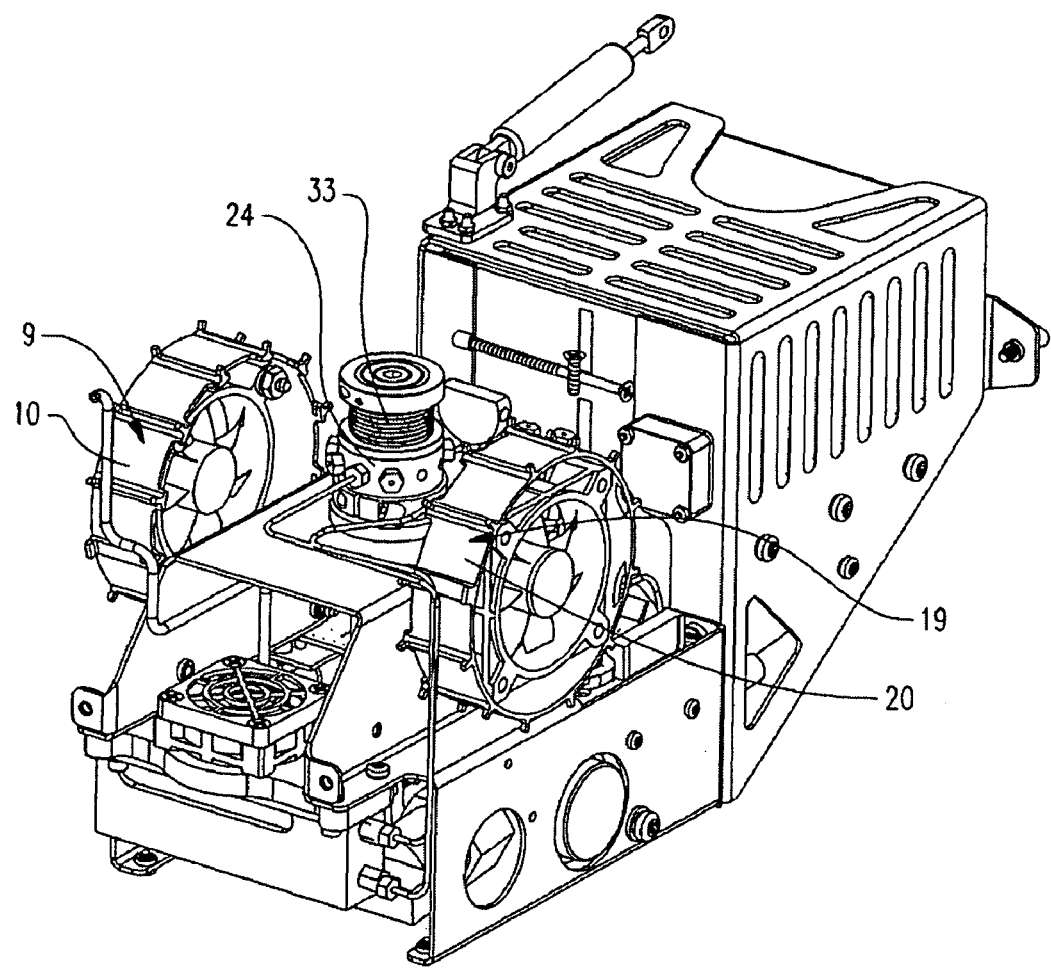
FIG. 8 is an end view of a gas chromatograph according to the invention with interior parts exposed.

FIG. 8 is an end view of a gas chromatograph according to the invention with interior parts exposed. GCCA's 9, 19 each include a GC column 10, 20. A multiport valve 24 is located between and is in communication with GC columns 10, 20 Sample loop 33 is clearly visible above the multiport valve 24.

Figure 9:
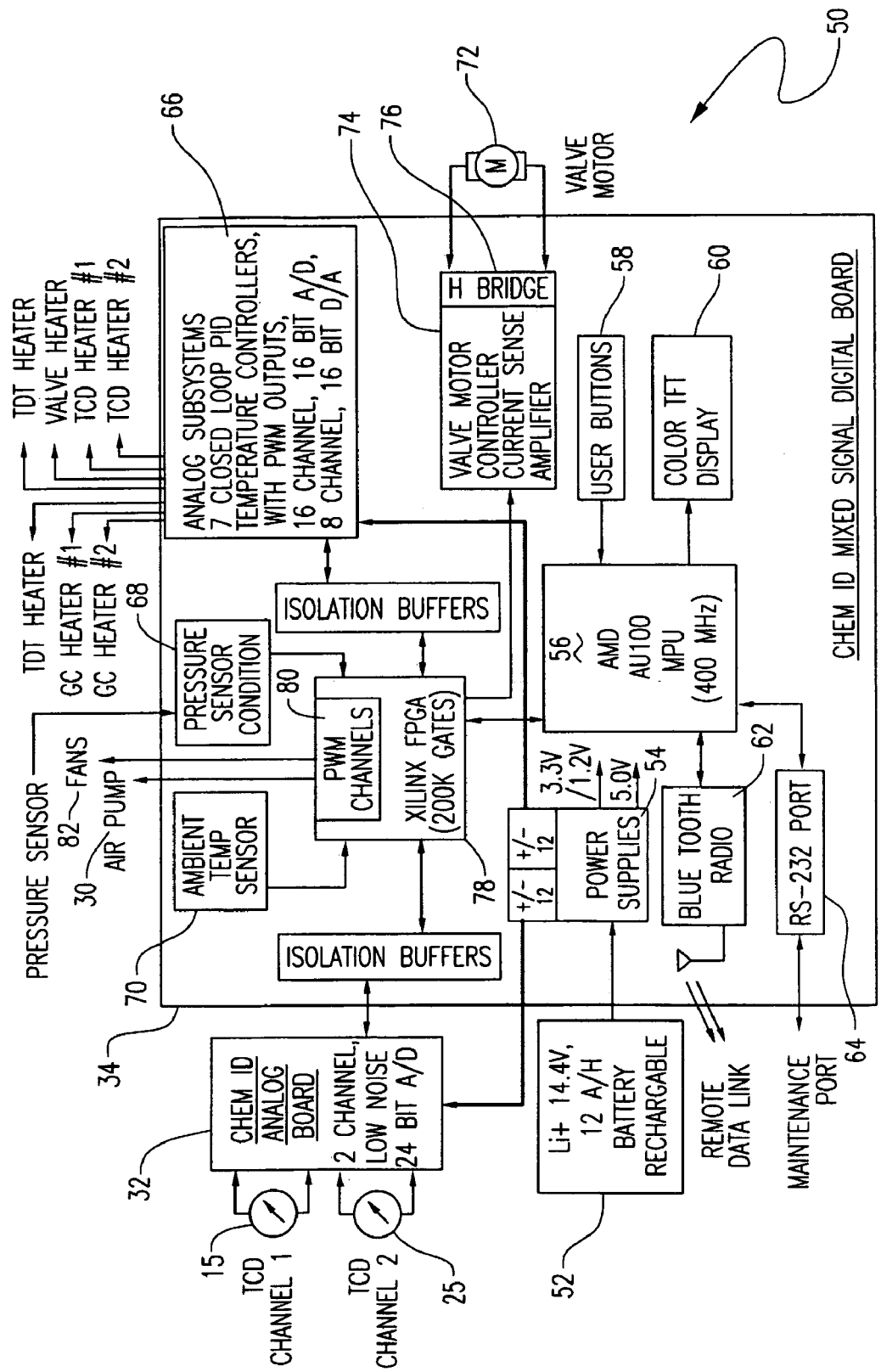
FIG. 9 shows a block diagram schematic of the electrical portion of the portable gas chromatograph system.

FIG. 9 shows a block diagram schematic of the electrical portion 50 of the portable gas chromatograph system. The system is powered by a 14.4 volt rechargeable Lithium battery 52, in an embodiment of the invention, although any commercially available battery could be utilized with the system, if desired. Battery 52 supplies power to power supplies 54, which after suitable conditioning, provide power to the various electronic components of the system. Either an AC or a DC power system is employed for driving the electronics, heaters and detectors in the system. The analog board 32, which is also referred to in FIG. 2 as the signal conditioning system 32, controls and calibrates the detectors 15 and 25. The digital board 34, which is also referred to in FIG. 2 as the digital processing system 34, converts the very small (microvolts) analog signals output by analog board 32 into accurate digital signals. The Central Processing Unit (CPU) 56 is programmed to perform signal processing to build a signature of the sampled chemical and identify the constituent chemicals, if present in the identification database, which is stored in Flash non-volatile memory which is loaded into RAM for real-time processing when the CPU 56 boots up. The measurements made in the field are also stored in the RAM in real-time and then written to the Flash memory as a background operation. The CPU 56 is also programmed to maintain the identification database, interact with the operator controls 58, and displays data on the display 60, such as the chemical identified. The system also has the capability to wirelessly communicate with an external computer via a remote data link, which can be any desired wireless link, but in an embodiment is a BlueTooth radio link 62. The BlueTooth radio link 62 allows wireless communication with an external computer up to 100 meters away from the portable system. Link 62 allows the detected chemical signature to be sent to the external computer for emailing to any desired person(s) or system(s). A maintenance port 64 is provided to allow an external system to be connected to the electronics, and in an embodiment the maintenance port is an RS-232 port. The analog systems section 66 portion of digital board 34 provides seven closed loop PID (Proportional, Integral, Derivative) control loops for controlling the TDT (Thermal Desorption Tube i.e. the Preconcentrator) Heater; the two GC heaters; the two TCD heaters; the valve heater (which heats valve 24) and the TDTT heater, which heats the TDT transfer line.

As air is sucked through the Preconcentrator/TDT 24, gas molecules are trapped in the storage chemical inside. Once enough sample is collected, the outside air flow is stopped, the Preconcentrator TDT Heater turns on and heats the Preconcentrator/TDT for a short period of time. This heat boils off the trapped molecules and releases a cloud of concentrated sample molecules. This cloud is what is transferred into the GCs 10 and 20. The TDTT heater mildly heats the transfer lines around the Preconcentrator/TDT 24 so that the hot gases released by heating the Preconcentrator/TDT 24 do not immediately condense in the colder pipes around the TDT 24. Analog systems section 66 also includes the temperature controllers with PWM (pulse width modulated) outputs, a 16 channel 16 bit analog to digital converter and an 8 channel 16 bit digital to analog converter. Pressure sensor condition 68 is connected to the pressure sensor of regulator 18 (discussed in more detail further below). Ambient temperature sensors 70 are provided. Valve motor 72 is connected to the valve motor controller 74 via H. Bridge 76, as is well known in the art. Valve controller 74 controls the position of the 10 port two position valve 24. A FPGA peripheral controller/data formatter is shown at 78 and pulse width modulated motor controllers are shown at 80, which control air pump 30 and fans 82.

Figure 10:
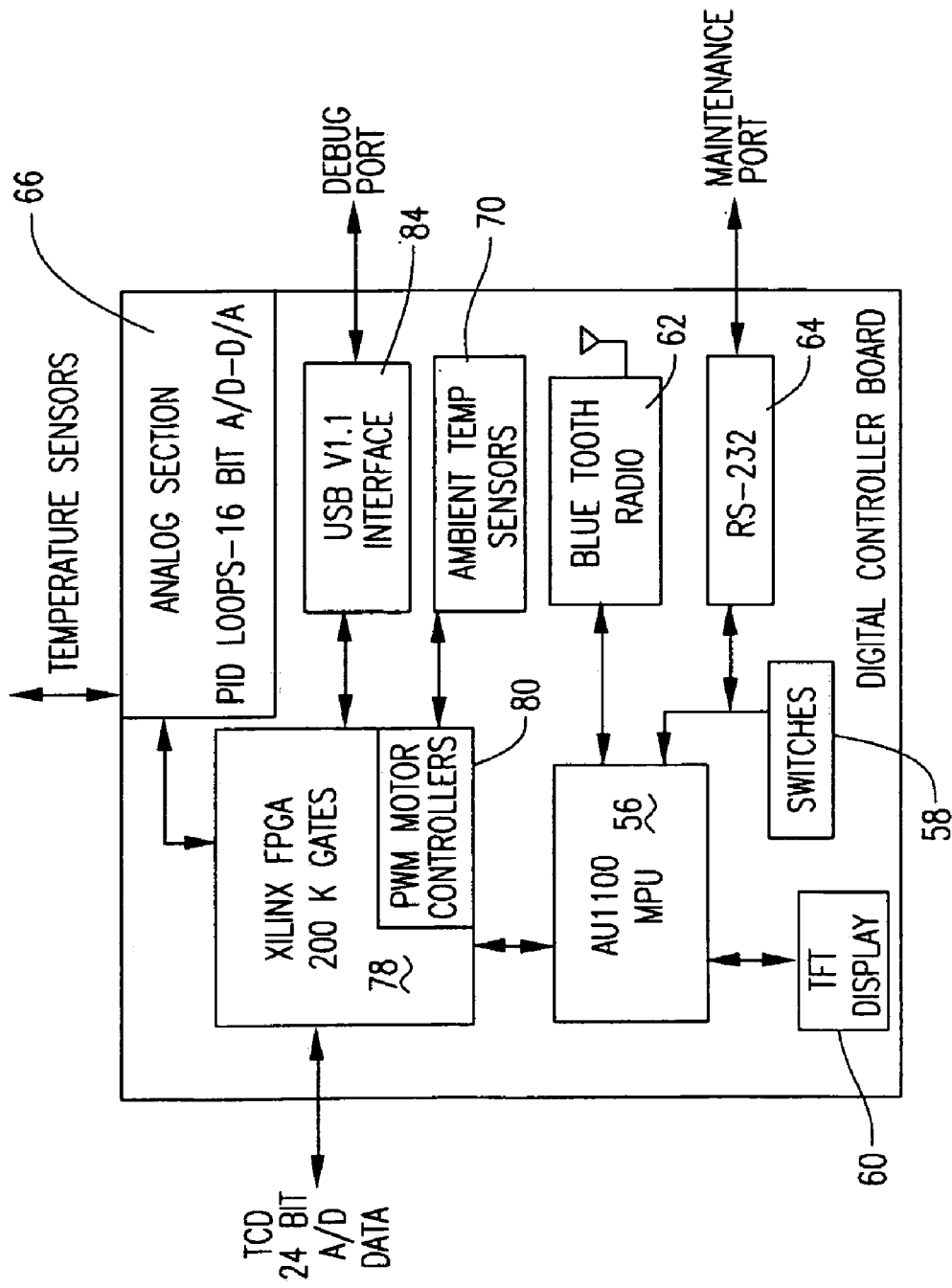
FIG. 10 shows a block diagram of the digital circuitry of the digital board.

FIG. 10 shows a block diagram of the digital circuitry of digital board 34. The ambient temperature sensors 70 receive temperature inputs from the various subsystems, such as the GC columns 9 and 19, the detectors 15 and 25 etc. The temperature sensors are in turn input to the PWM motor controllers 80, which control the air pump 30 and fans 82. This block diagram also shows a debug port provided to the digital board 34, which in an embodiment is a USB port 84.

Figure 11A:
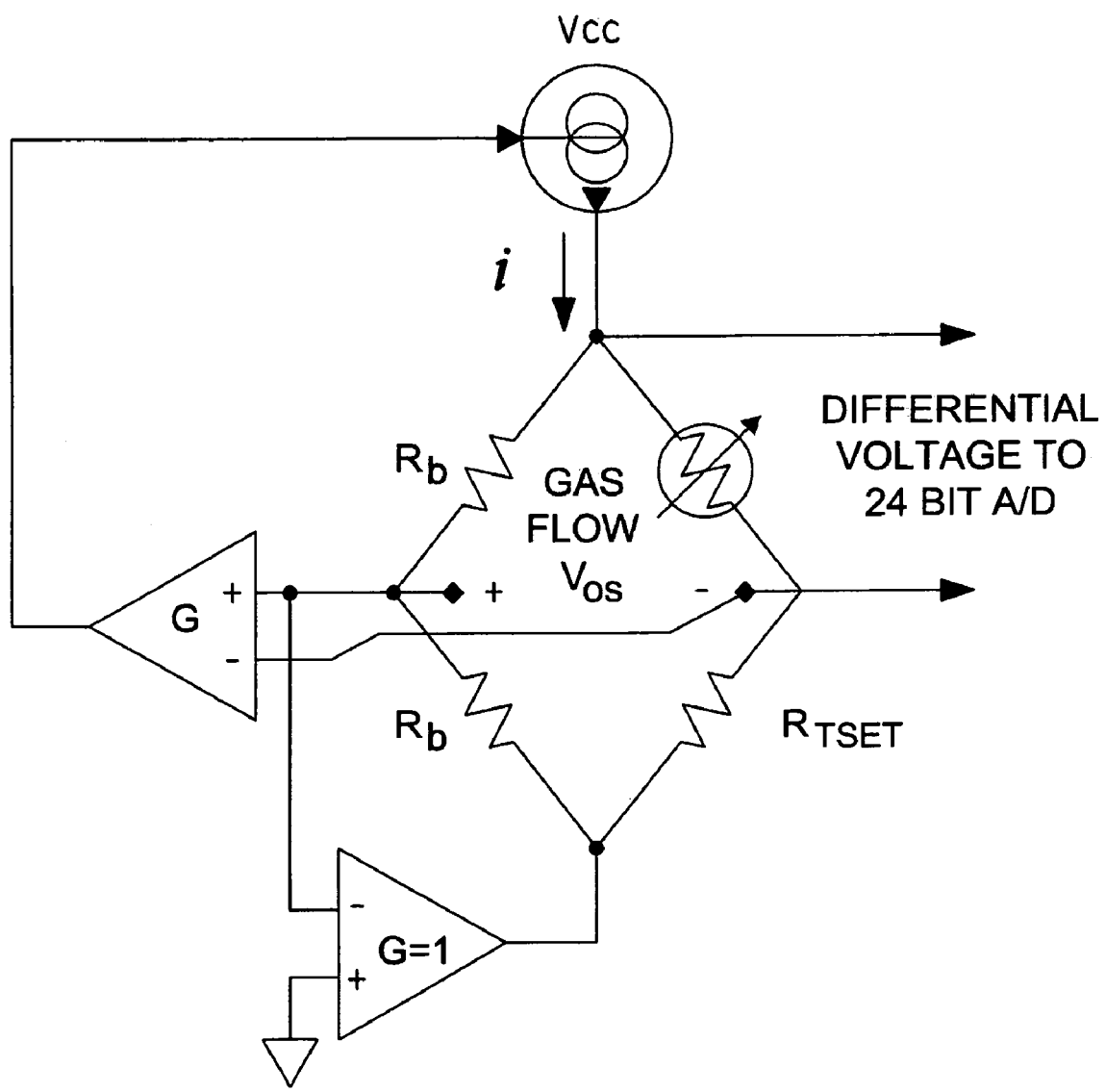
FIG. 11A is an electrical circuit schematic showing the TCD bridge analog to digital circuit.

FIG. 11A is an electrical circuit schematic showing the TCD bridge analog to digital circuit. In some embodiments, two TCD bridge circuits are provided, to connect the two TCD detectors 15 and 25 to the FPGA peripheral controller/data formatter 78.

Figure 12:
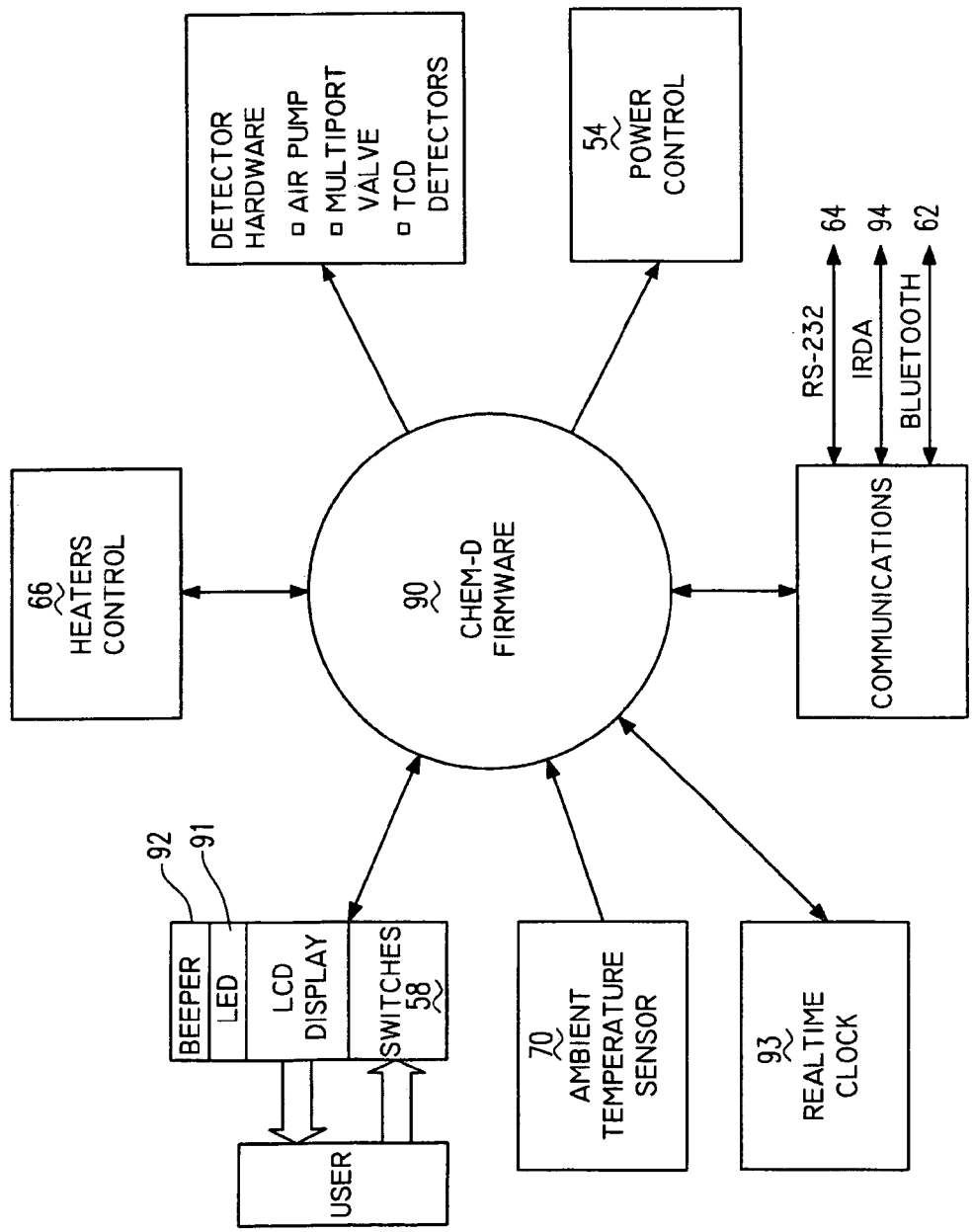

FIG. 12 shows a system firmware context diagram, which shows that the Chem-ID firmware 90 interacts with the user via switches (or buttons) 58 and via display 60. The system firmware can also interact with a user via LED 91 or beeper 92, as well as by emailing a user using BlueTooth radio link 62 and an external computer which is connected to the internet. The ambient temperature sensors 70 input their temperatures to the firmware 90. A real-time clock 93 interacts with firmware 90. The firmware 90 interacts with the heaters control 66. The firmware 90 controls the detector hardware, namely the air pump 30, the multiport valve 24 and the TCD detectors 15 and 25. The firmware 90 controls the power control 54. The firmware 90 interacts with the communications subsystems, namely the maintenance port 64 an IrDA port 94 and the Bluetooth data link 62.

Gas Chromatograph Column Assembly

Figure 13:
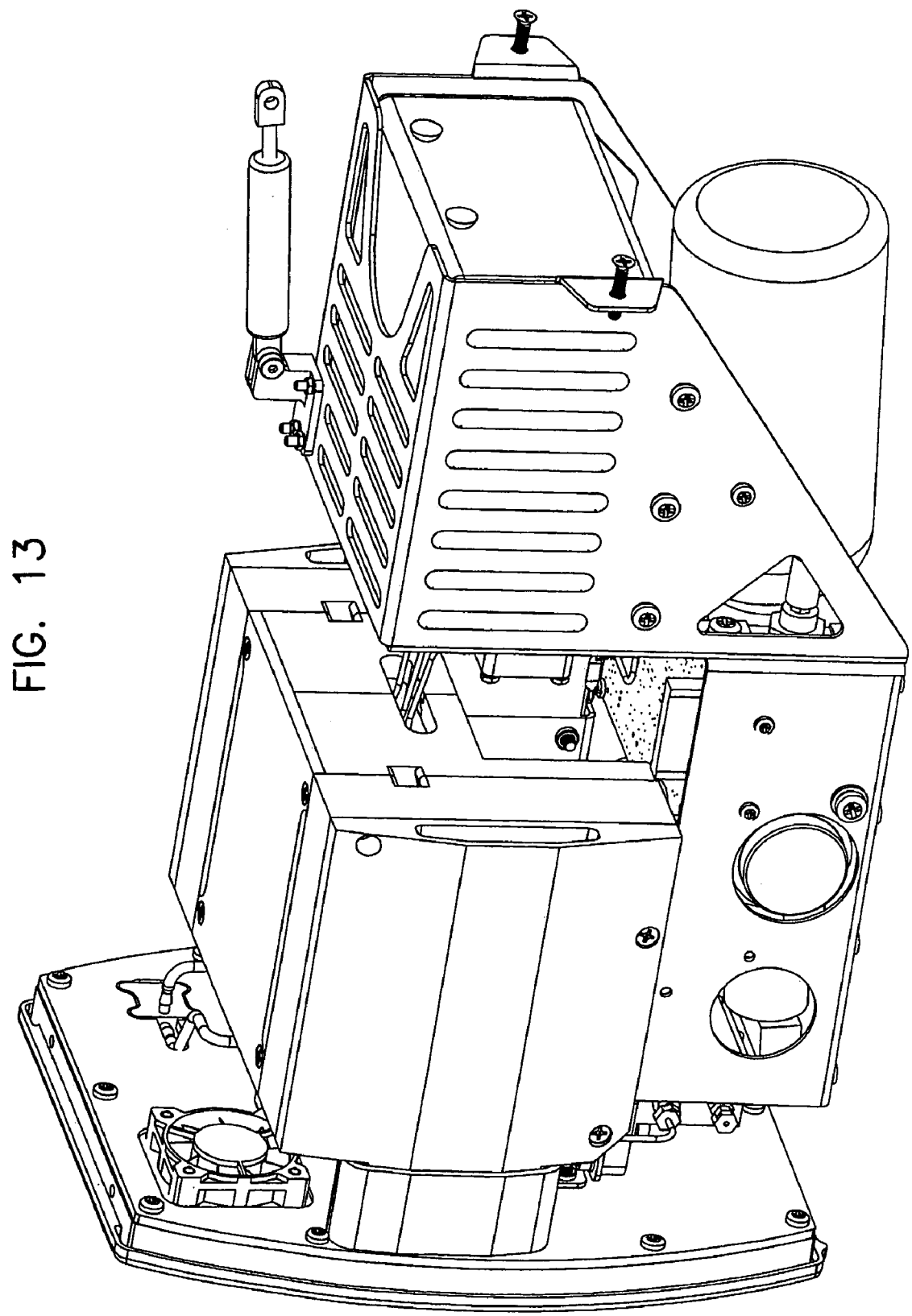
Figure 14:
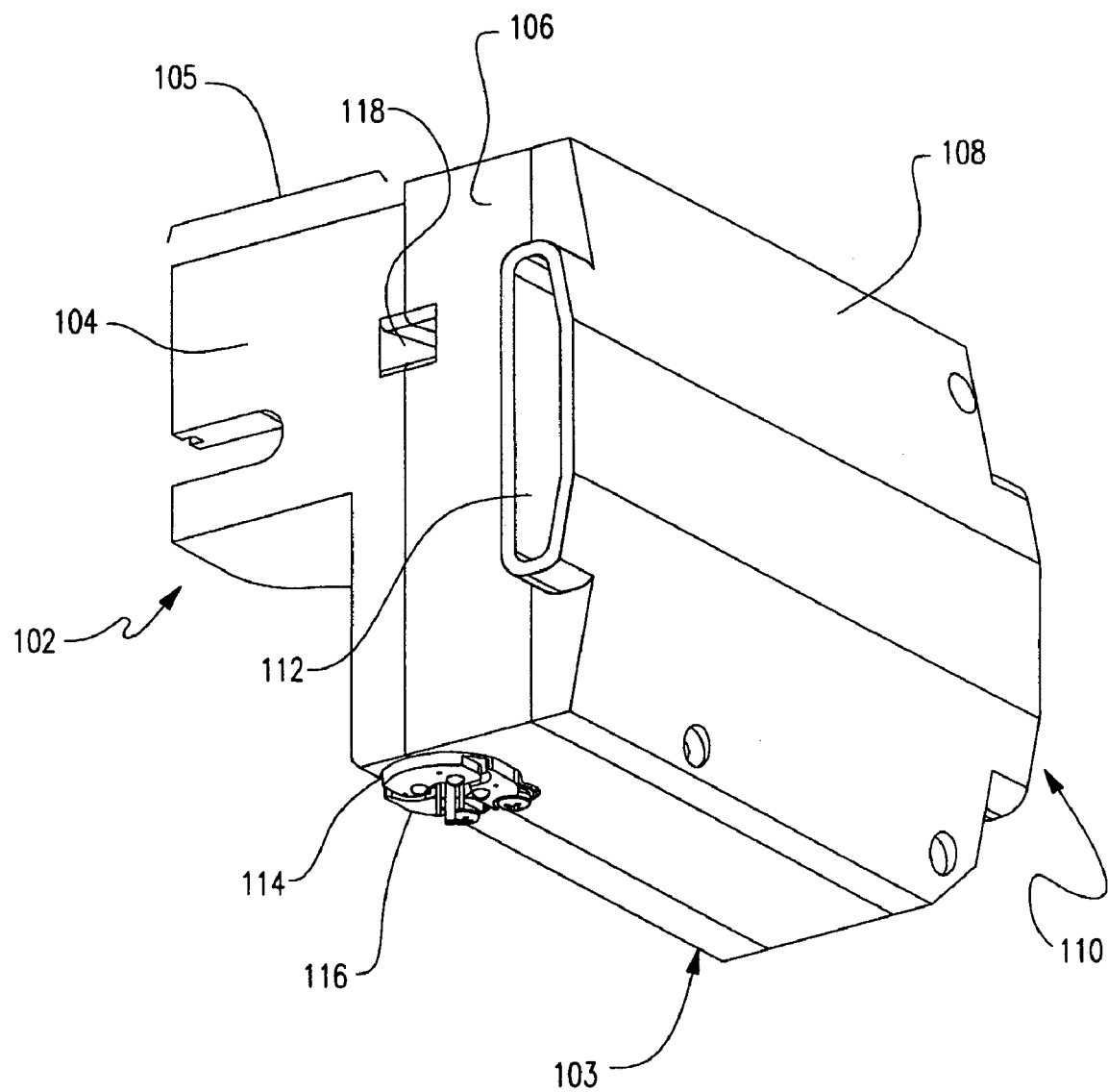
Figure 15:
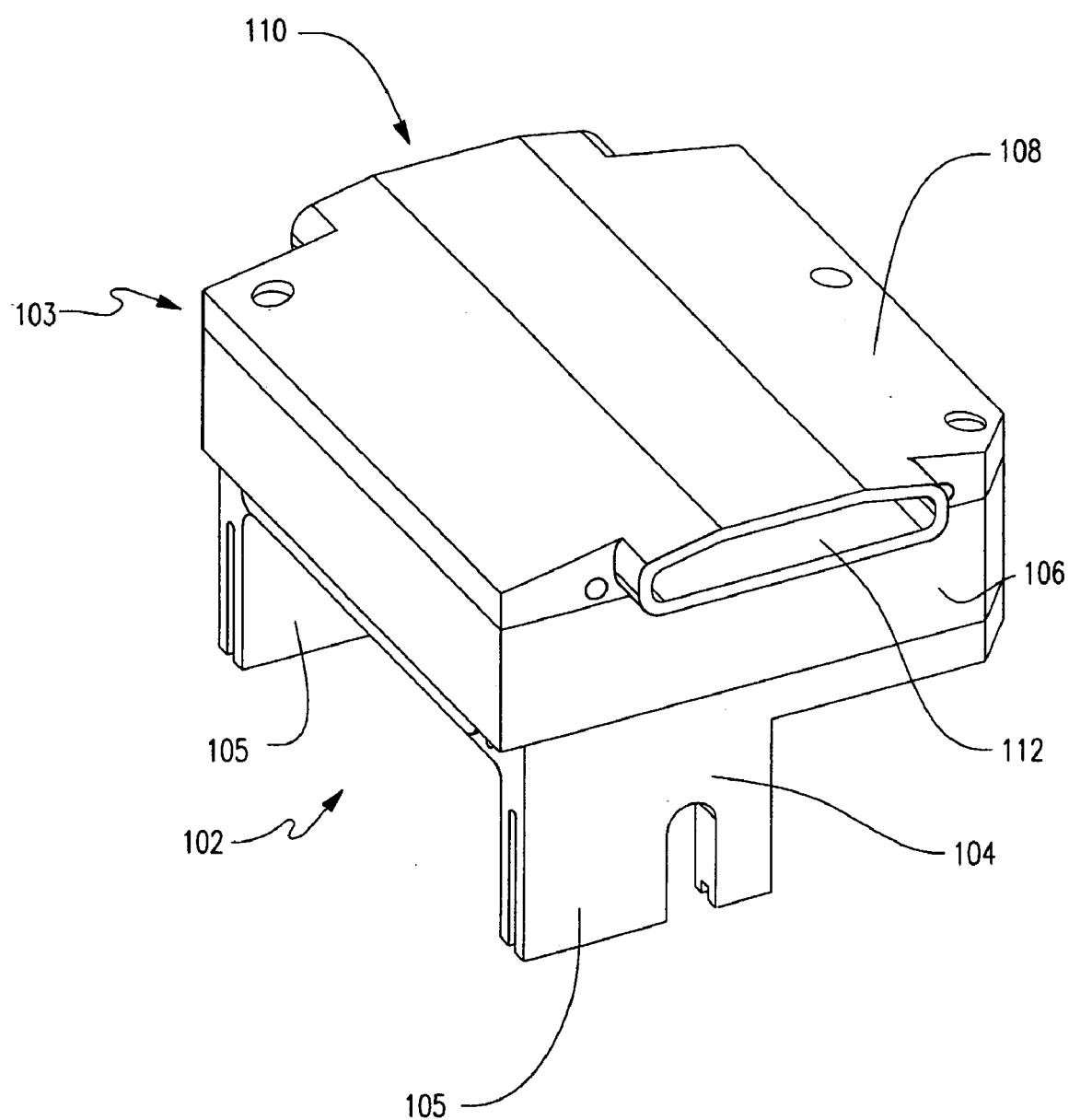

FIG. 13 illustrates an embodiment of a gas chromatograph with interior parts visible. In particular, a gas chromatograph column assembly as described below can be seen in the interior. FIGS. 14-26 illustrate an embodiment of the Gas Chromatograph Column Assembly (GCCA) 102. The GCCA 102 is utilized in the over all system described herein. FIGS. 14-15 show different perspective views of the GCCA 102. The GCCA 102 has a housing 103 that houses a separation column 10 or 20. The housing 103 includes an insulated valve housing 104, a column housing 106 and a port plate 108 fitted together. The port plate 108 defines an intake port 110 and an exhaust port 112. The insulated valve housing 104 and the column housing 106 define an opening 114 to receive a detector 116 and an inlet port 118 to receive a sample to be tested.

Figure 23:
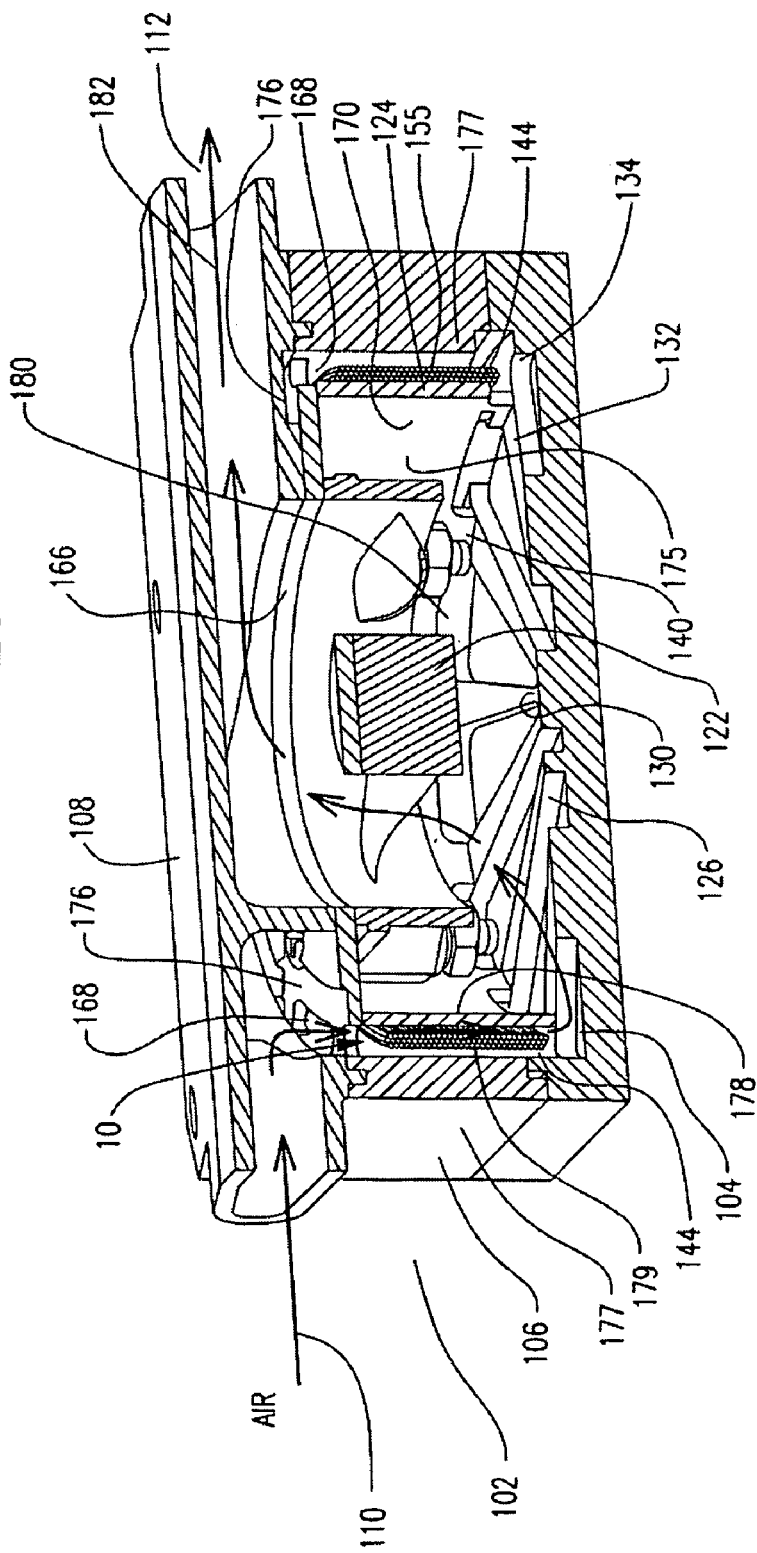

The valve housing 104 housing functions as a bottom plate of the GCCA 102. However, extensions 105 from a left hand GCCA 102 (FIG. 14) cooperate with extensions 105 from a right hand GCCA 102 (FIG. 15) to form a housing and insulation for the rotary valve for the overall GC System. As mentioned above, the overall GC System includes a left hand GCCA and a right hand GCCA. One includes separation column 10 and the other includes separation column 20. The discussion herein applies to both. It should be understood that the extensions 105 may be excluded when discussing the GCCA 102 as a stand alone unit, such as shown in FIG. 23.

Figure 16:
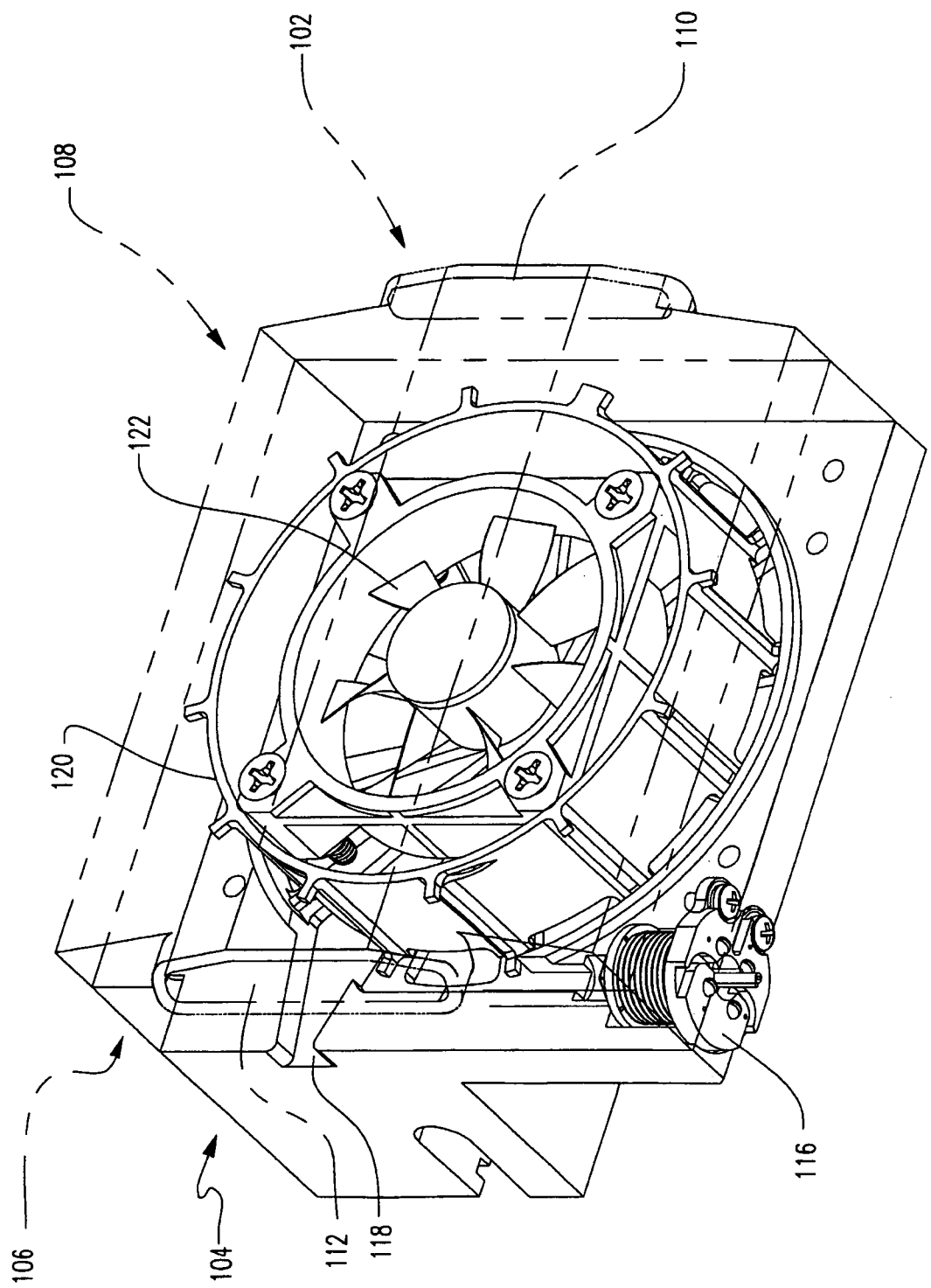

FIG. 16 shows the GCCA 102 with the column housing 106 and port plate 108 being transparent to reveal the column and support structure 120, a cooling fan 122, such as, but not limited to, a forced convection (fan), and the detector 116. A sample to be analyzed is introduced into an end of the column 10 through the inlet port 118. The detector 116, which is connected to the remaining end of the column, detects the exiting sample.

Figure 17:
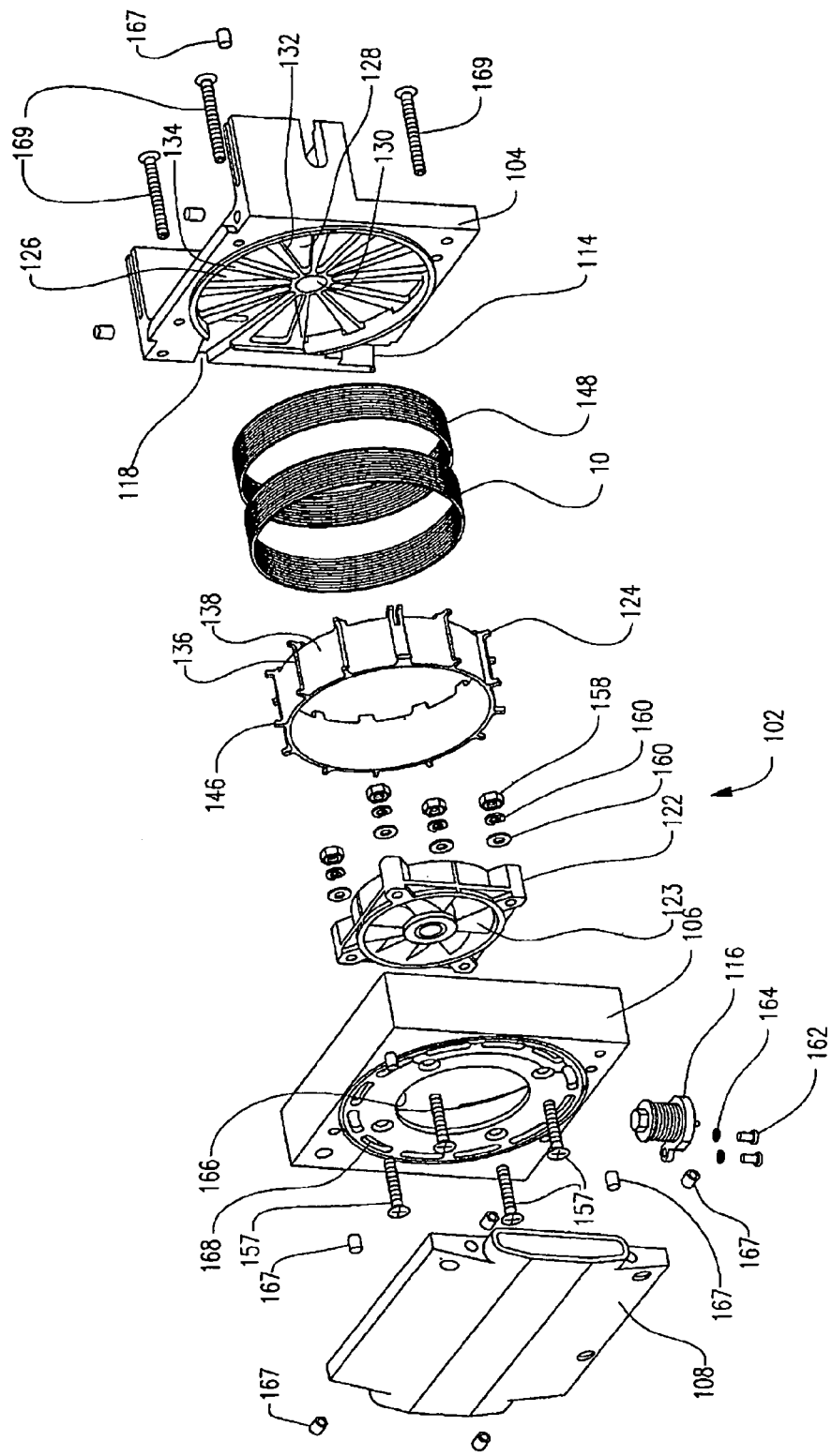
Figure 18:
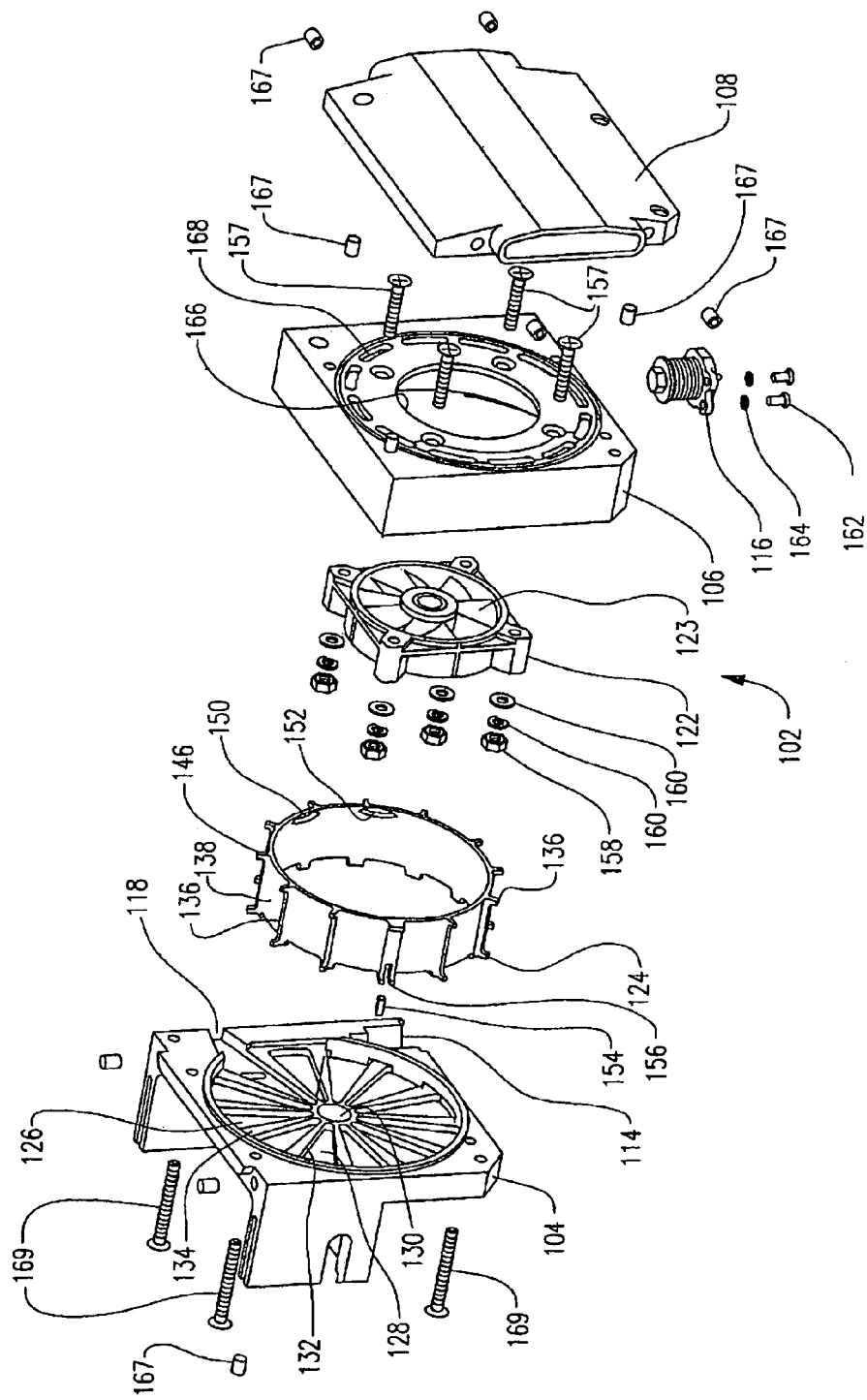

FIGS. 17 and 18 show blow-up views of the GCCA 102 showing the GCCA's 102 construction and arrangement. FIG. 17 shows a left hand GCCA 102 and FIG. 18 shows a right hand GCCA 102. The left hand and right hand GCCAs 102 differ only in that the inlet port 118, the detector opening 114 and the intake 110 and exhaust 112 ports are on opposite sides.

As shown in FIGS. 17 and 18, the valve housing 104 is configured to receive the column support 124. The central portion 126 of the valve housing 104 has wells 128 circumferentially dispersed around a center portion 130. The wells 128 are separated by raised portions 132 that extend from the center portion 130 to a periphery 134 of the central portion 126. As, can be seen in the figures, portions 118, 114, are also configured to form the inlet port 118 and the detector opening 114.

In some embodiments, the valve housing 104 is made from low density rigid foam, such as, but not limited to, light weight polymethacrylimide. In one embodiment, the valve housing 104 is made from Rohacell RIMA 71 composite foam. Such materials provide a high degree of insulation and resist high temperatures. The valve housing 104 is formed by suitable means, including, but not limited to, machining and molding.

Figure 19:
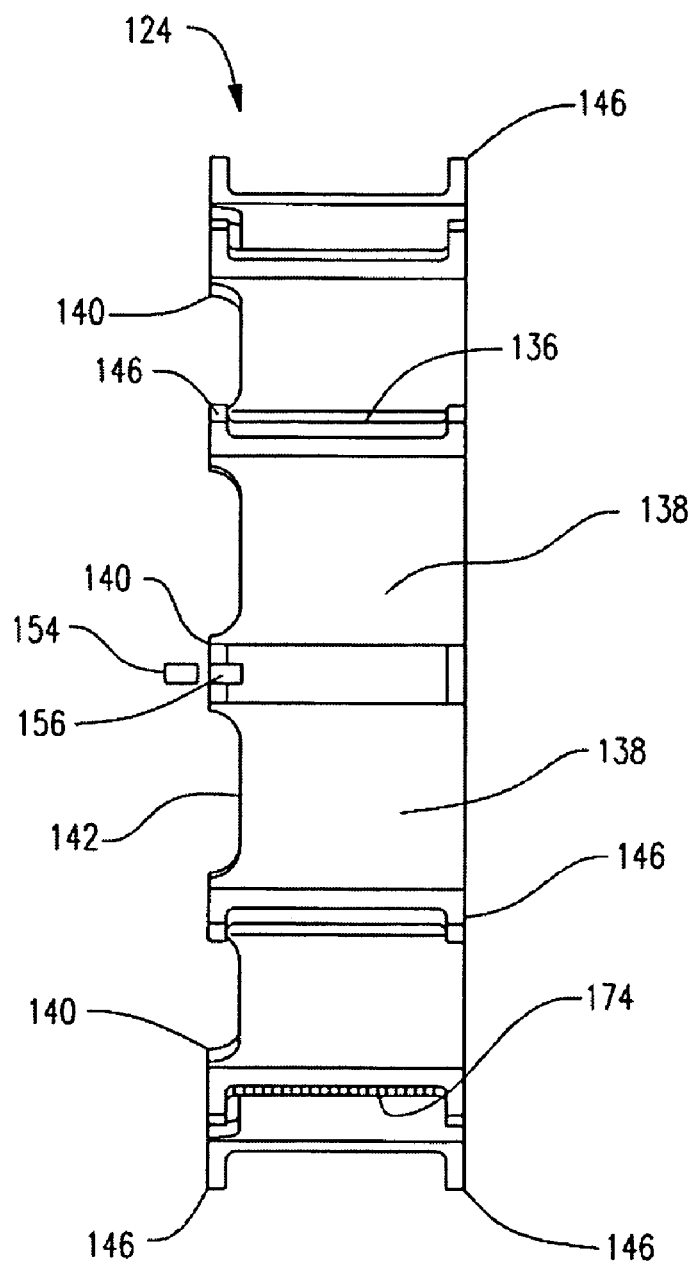

The column support 124 sits in the central portion 126 of the valve housing 104. As shown in FIG. 19, the column support 124 is ring-shaped and has circumferentially spaced bridges 136 extending the width of the column support 124. The bridges 136 are raised from the outer surface 138 of the column support 124 and extend laterally from one of the side edges 142 of the column support 124 to form lateral posts 140.

In some embodiments, the column support 124 is made from low density rigid foam, such as, but not limited to, light weight polymethacrylimide. In one embodiment, the column support 124 is machined from a slab of Rohacell RIMA 71 composite foam. Such materials provide a high degree of insulation and resist high temperatures.

The tubing 144 that makes up the separation column 10 is wrapped around the column support 124, resting only on the bridges 136. The bridges 136 include radially extending end posts 146 that bookend the wrapped tubing 144. The radially extending end posts 146 extend above the wrapped tubing 144. In some embodiments, the top surface 174 of the bridges 124 is threaded so as to receive individual windings of tubing 144 and serves to further limit movement of the tubing 144 on the bridges 136.

As shown in FIG. 17, the separation column 10 is wrapped around the column support 124. This combination, in turn, is optionally wrapped with insulation 148. An example of the insulation includes, but is not limited to, a polyamide tape. The combination is set in the valve housing 104 with the lateral posts 140 of the column support 124 resting on the raised portions 132 of the central portion 126 of the valve housing 124.

The column support 124 also includes openings 150 and 152. 150 and 152 are holes that allow the ends of column tubing 144 to leave the column support 124. As shown in FIGS. 18 and 19, the column support 124 includes a slot 156 to receive a temperature sensor 154 to monitor the temperature of the column 10.

Figure 20:
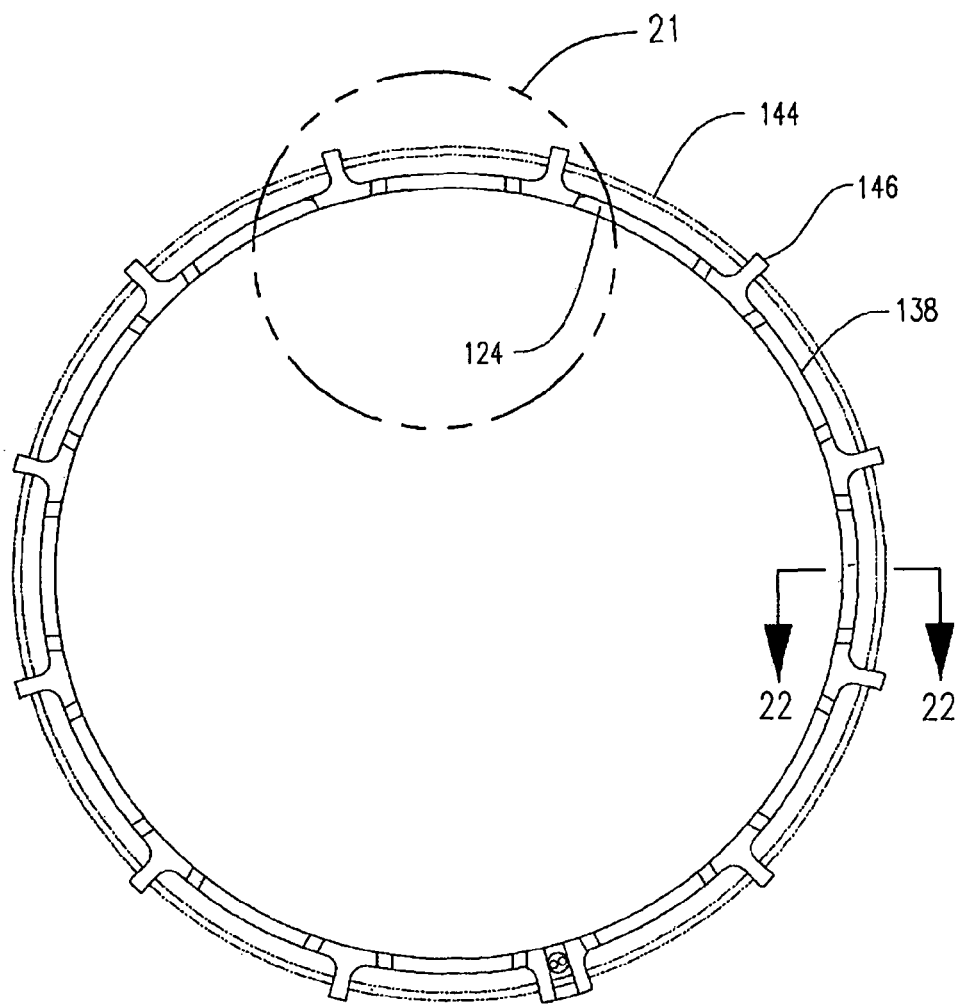
Figure 21:
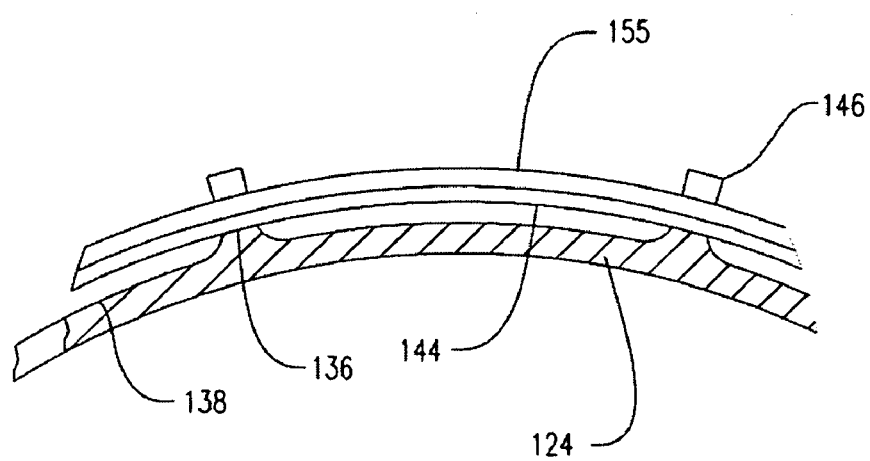

FIG. 20 shows a side view of the column support 124 cleaved along its circumference. FIG. 21 shows a blown up partial view of FIG. 20. As can be seen, the tubing 144 is wrapped around the column support 124 and rests on the bridges 136 between the radially extending end posts 146 of the bridges 136.

Returning now to FIGS. 17 and 18, the cooling fan 122 is position within and is connected to the column housing 106 via suitable means. In the embodiment shown, the cooling fan 122 is attached to the column housing 106 via screws 157, nuts 158 and washers 160. The column housing 106 is then positioned over the column support 124 and on the valve housing 104, enclosing the column support 124 and the cooling fan 122.

The column support housing 106 includes a central opening 166 positioned over the fan blades 123 of the cooling fan 122, which is positioned at least in part within the circumference of the column support, so as to allow heated air drawn up by the cooling fan to vent. A plurality of intake vents 168 is dispersed in the column housing 106 around the central opening 166. When the column housing 106 is positioned over the column support 124 and on the valve housing 104, the intake vents 168 are position at least in part outside of the circumference defined by the of the outer surface 138 of the column support 124.

In some embodiments, the column support housing 106 is made from low density rigid foam, such as, but not limited to, light weight polymethacrylimide. In one embodiment, the column support housing 106 is made from Rohacell RIMA 71 composite foam. Such materials provide a high degree of insulation and resist high temperatures. The column support housing 106 is formed by suitable means, including, but not limited to, machining and molding.

The detector 116 is positioned within the detector opening 114 formed between the valve housing 104 and column housing 106 and is secured via suitable means. In the embodiment shown, the detector 116 is attached via screws 162 and split lock washers 164.

The port plate 108 is positioned over the column housing 106 and secured to the valve housing 104 and the column housing 106 by suitable means. In the embodiment shown, it is secured via threaded inserts 167 and screws 169 as shown.

In some embodiments, the port plate 108 is made from low density rigid foam, such as, but not limited to, light weight polymethacrylimide. In one embodiment, the port plate 108 is made from Rohacell RIMA 71 composite foam. Such materials provide a high degree of insulation and resist high temperatures. The port plate 108 is formed by suitable means, including, but not limited to, machining and molding.

Figure 22:
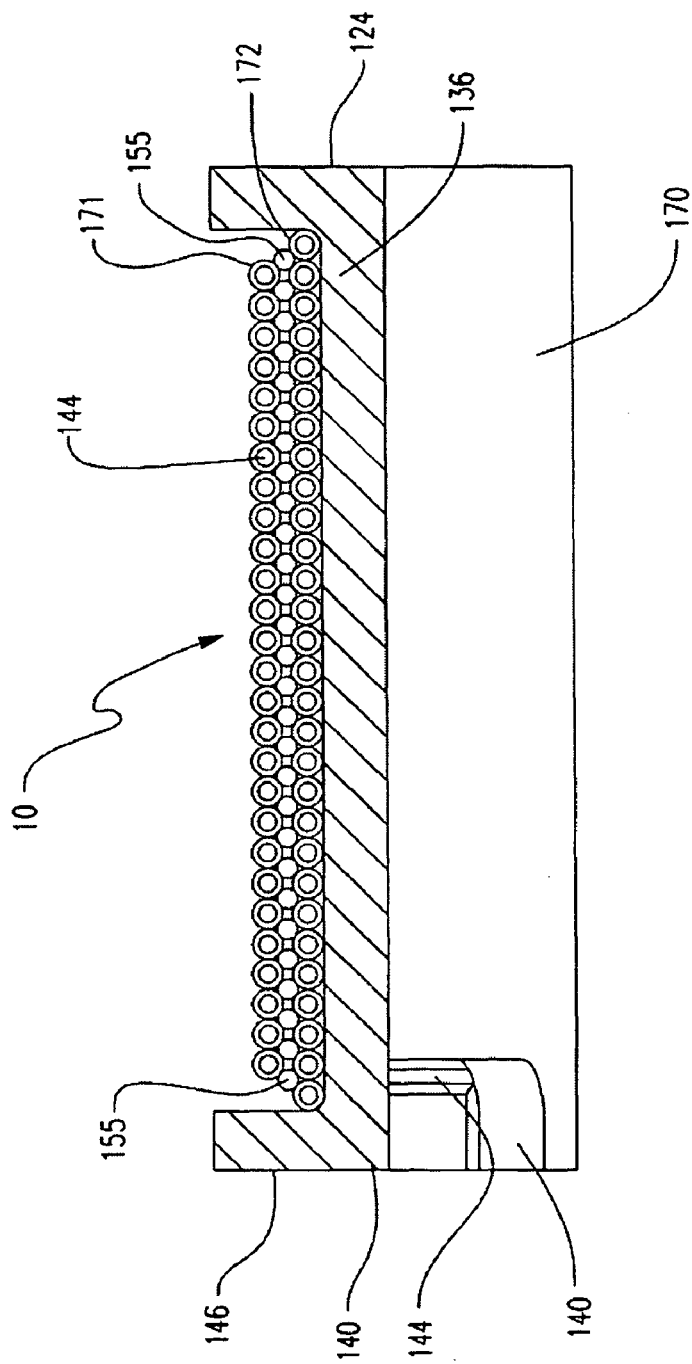

FIG. 22 shows a partial cross-section of the column support 124 along lines 19B-19B of FIG. 19. The cross-section is cut through one of the bridges 136. The column support 124 extends downward back into the page showing the inner surface 170 of the column support 124. In the embodiment shown, the tubing 144 that makes up the column 10 extends around the column support 124 forming two rows 171, 172. Resistive heat wire 155 is wrapped between and is in contact with the rows 171, 172, of tubing 144. The resistive heat wire is in contact with a power source and is used to heat the column 10. It should understood that there may be one or more rows of tubing depending upon the length of the column tubing 144 and/or the width of the column support bridges 124.

As mentioned above, in some embodiments, the top surface 174 of the bridges 124 is threaded so as to receive individual windings of tubing 144 and serves to further limit movement of the tubing 144 on the bridges 136. This maintains the geometry between the coils of the wrapped column tubing 144 and the heating wire and fixes them with respect to each other over the entire length of the column. This maintains uniformity and accurate heating of the column 10 to producing accurate and repeatable measurements.

FIG. 23 is a cut away illustration showing the inner chamber 175 of the GCCA 102. As can be seen, the port plate 108 and the support column housing define an intake chamber 176. The intake chamber 176 is in fluid communication (including gaseous communication) with and receives outside air from the intake port 110. The intake chamber 176 extends 360° around the central opening 166 of the support chamber housing 106. Air is drawn into the intake chamber 176 by the cooling fan 122 and down through the intake vents 168 of the support chamber housing. As shown in FIG. 23, the cooler air is drawn down over the column tubing 144, which is positioned between the side walls 177 of the column support housing 106 and the outer surface 138 of the column support 124. Since the column tubing 144 is raised above the outer surface 138 by the bridges 136 and separated from the side walls 177 of the column support housing 106 by the radially extending end posts 146, the cooling air travels over the inner 178 and outer 179 surfaces of the column 10.

Figure 24:
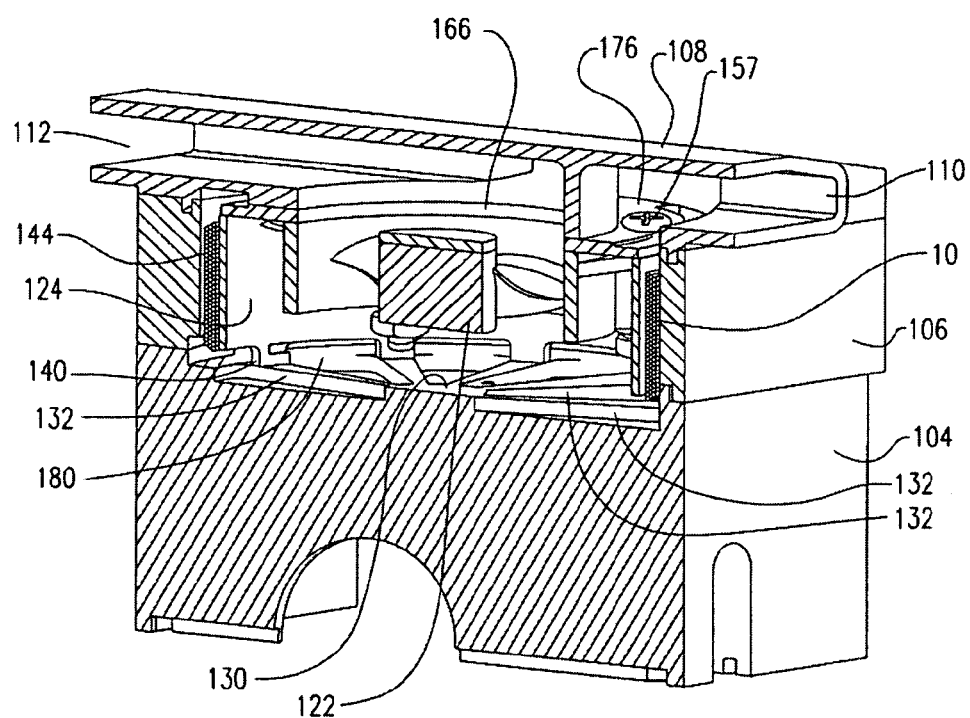
Figure 25:
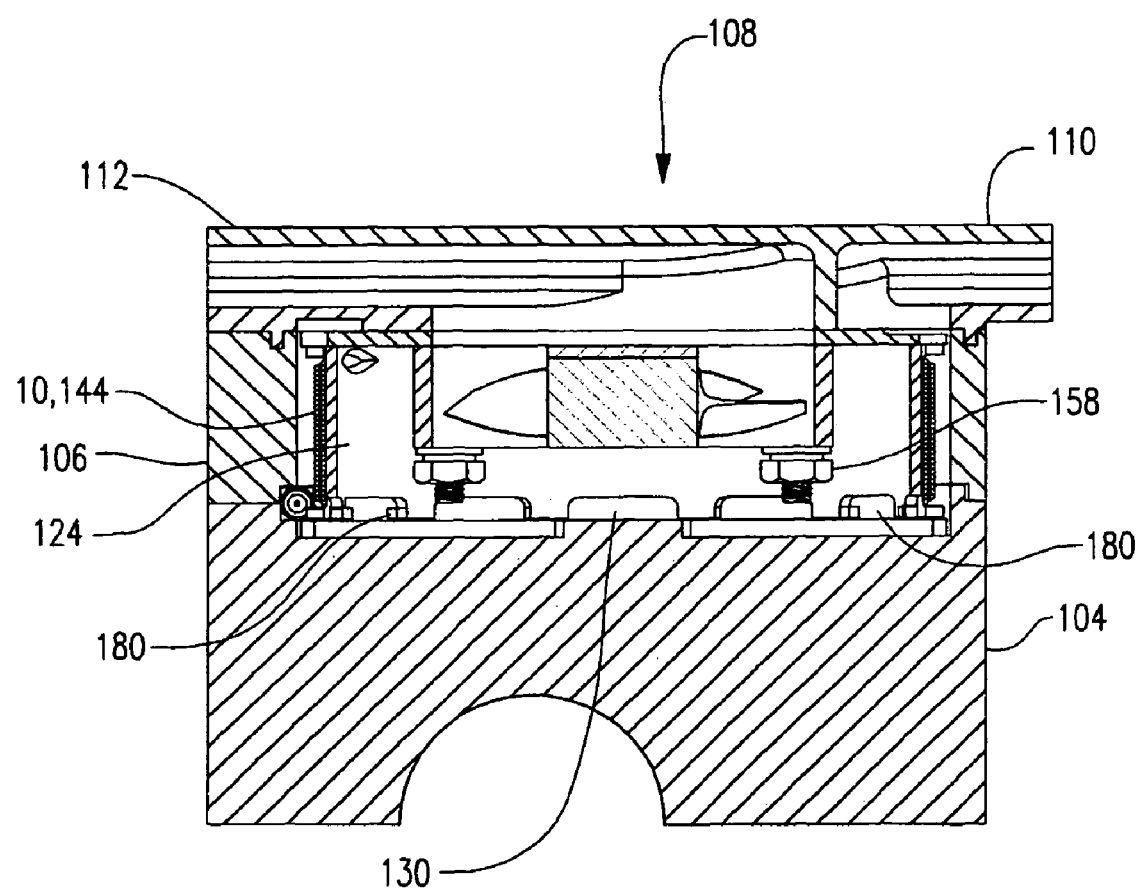

As can be seen in FIG. 23, the lateral posts 140 of the support column 124 sit on the raised portions 132 of the valve housing 104 forming exhaust vents 180 allowing the intake chamber 176 to be in fluid communication with the inner chamber 175. The air that is drawn down over the column 10 is allowed to escape into the inner chamber 175 through the exhaust vents 180. As the air passes over the heated column tubing 144 and resistant heat wire 155, it is heated. The cooling fan 122 purges the hot air by drawing it into the inner chamber 175 and out through the central opening 166 of the column support housing 106 into an exhaust chamber 182 and out of the exhaust port 112. FIGS. 24 and 25 show further views of an embodiment of the GCCA 102.

The GCCA 102 allows for rapid cooling via forced convection (fan). The low thermal mass of the column 10, and the fact it is suspended in the air, support rapid cooling. The fan 122 draws air directly across the column 10 and exhausts through the center 166 of the system. This flow prevents heated air from flowing across any other part of the column 10 or column support 124.

The GCCA 102 is designed to allow columns of any material to be installed. Examples of usable column materials include, but are not limited to fused silica (i.e. glass) and stainless steel. In some embodiments of the invention, the column length is greater than or equal to 50 feet of capillary column. In other embodiments, the column length is greater than or equal to 52.5 feet capillary column. The GCCA 102 is constructed such that columns, such as columns made of stainless steel of such length, may be used in a form factor less then 3.25 inches in diameter while still maintaining integrated, precision heating.

Figure 26:
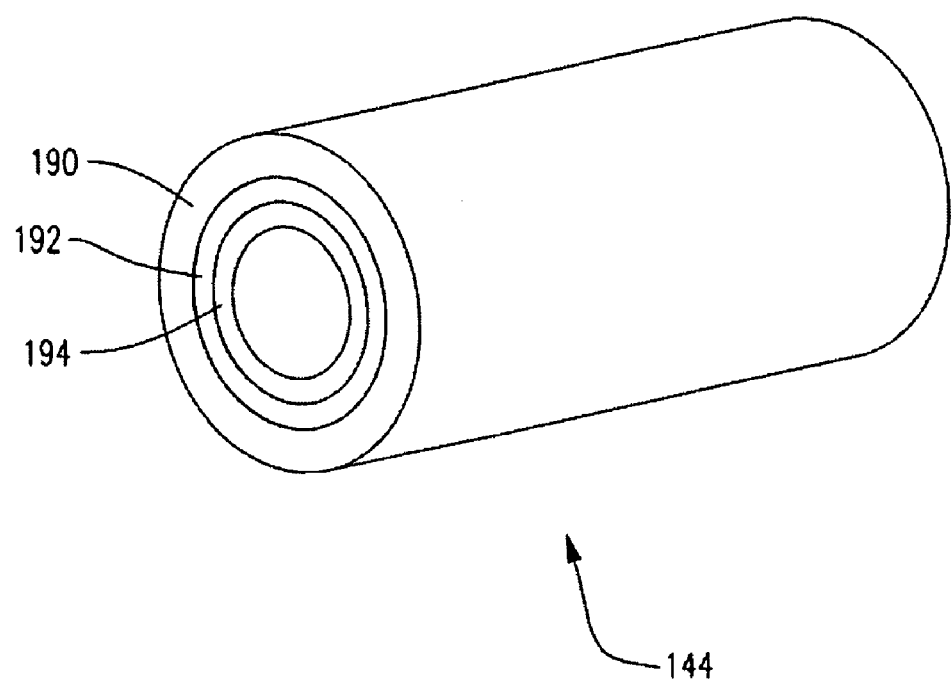

FIG. 26 illustrates a non-limiting example of a cross-section of column tubing. As shown, in some embodiments the column tubing 144 has a polyimide outer coating 190 surrounding a silica layer 192 which in turn surrounds a layer of stationary phase 194. Examples of stationary phases, in addition to the ones mentioned above, include, but are not limited to, polydimethylsiloxane (DB-1) and polyethylene glycol (DB-WAX).

In some embodiments of the invention, the column 10 is heated to over 200° C. within 2 minutes and back down to ambient temperature within 3 minutes.

In some embodiments, the resistive heat wire is coated with an insulation coating, such as, but not limited to, a polyamide coating.

In some embodiments, the design of the GCCA 102 is such that it may be in close proximity to electronic devices, such as those contained in the Portable Gas Chromatograph described herein, and the detector 116 without damaging the solder on electronic boards or affecting the accuracy of the detector 116.

In some embodiments of the invention, the GCCA 102 is less than 0.5 lbs and in one embodiment it is about 0.425 lbs. In some embodiments, the GCCA 102 is less than 5.50 inches long from inlet port 110 to exhaust vent 112, less than 3.6 inches wide from the outside edge of the housing to one half of the valve housing and less than 4.2 inches tall.

Compact Thermal Conductivity Detector

Figure 27:
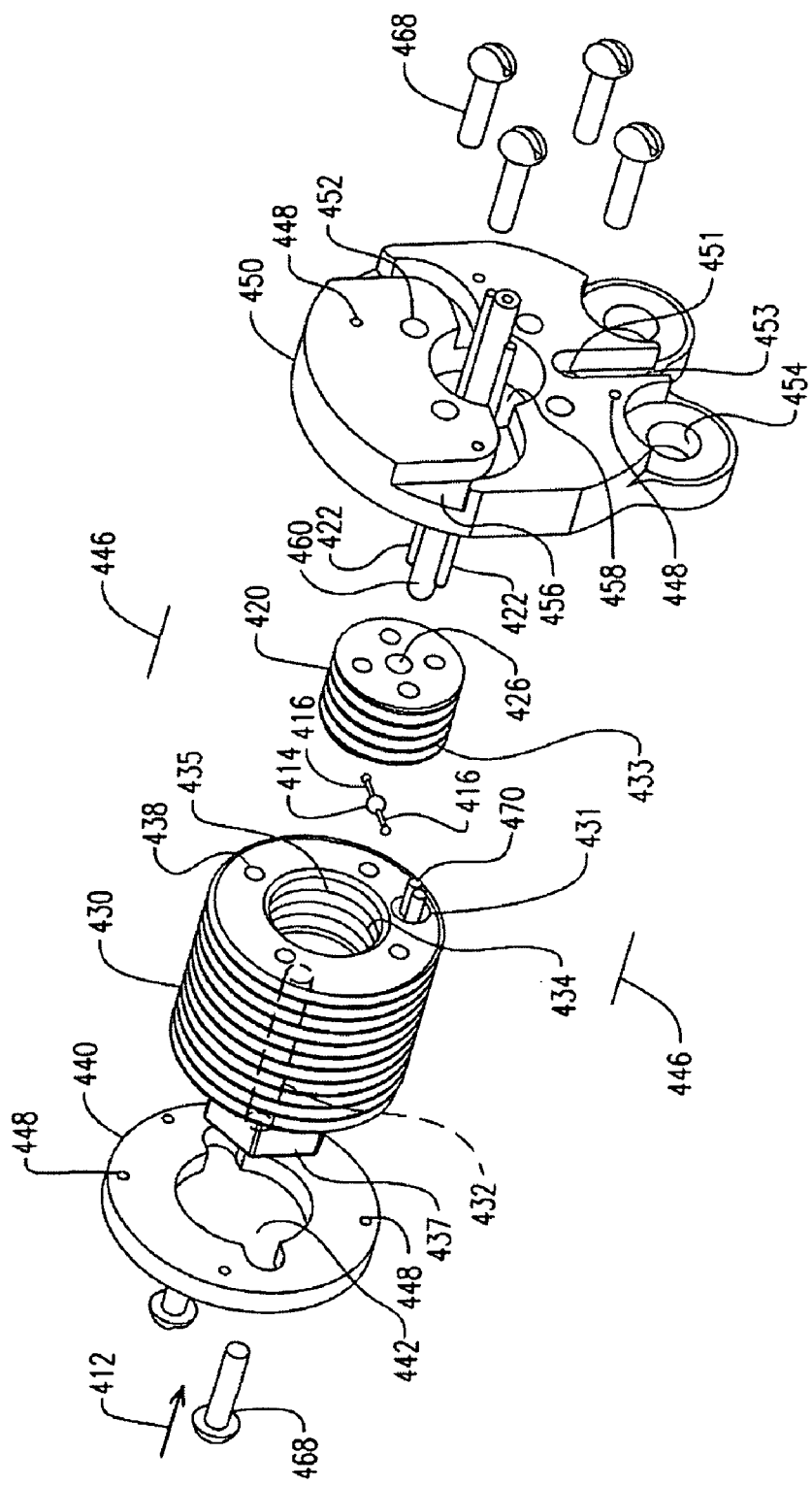

FIG. 27 shows an exploded view of an embodiment of a compact thermal conductivity detector 410 that is suitable for use as a detector 15 in various embodiments of a gas chromatograph 5 as described herein. The thermal conductivity detector 410 determines the thermal conductivity of a gas in a flowing gas stream by measuring the electrical resistance across a thermistor 414 as the gas stream being analyzed flows over the thermistor 414. As particles in the gas stream of varying size, density and/or molecular weight pass across the thermistor 414, the temperature of the thermistor 414 varies, thereby varying the resistance across the thermistor 414. The resistance is measured to a microvolt level of precision and is thus susceptible to errors induced by temperature fluctuations induced from outside of the detector 410. Therefore, the temperature of the detector 410 is controlled and regulated, and insulative materials are used in forming the detector 410 as described herein. In some embodiments, the detector 410 is manufactured such that any portions of the detector 410 in contact with the flowing gas stream are substantially chemically inert.

The detector 410 comprises the thermistor 414, a sensor housing 420, a body housing 430, a first end plate 440 and a second end plate 450. Contact pins 422 that pass through the sensor housing 420 are electrically attached to the thermistor 414 and comprise a portion of the thermistor 414 electrical circuit. Internal cavities in the sensor housing 420 and body housing 430 form a gas analysis chamber in which the thermistor 414 is located. The gas analysis chamber is shown in greater detail in FIG. 32. The flowing gas stream 412 to be analyzed enters the gas analysis chamber through a fluid inlet passageway 432 in the body housing 430. The gas stream exits the gas analysis chamber through a fluid outlet passageway 426 in the sensor housing 420 and a flow tube 460 in fluid communication with the fluid outlet passageway 426.

Figure 28:
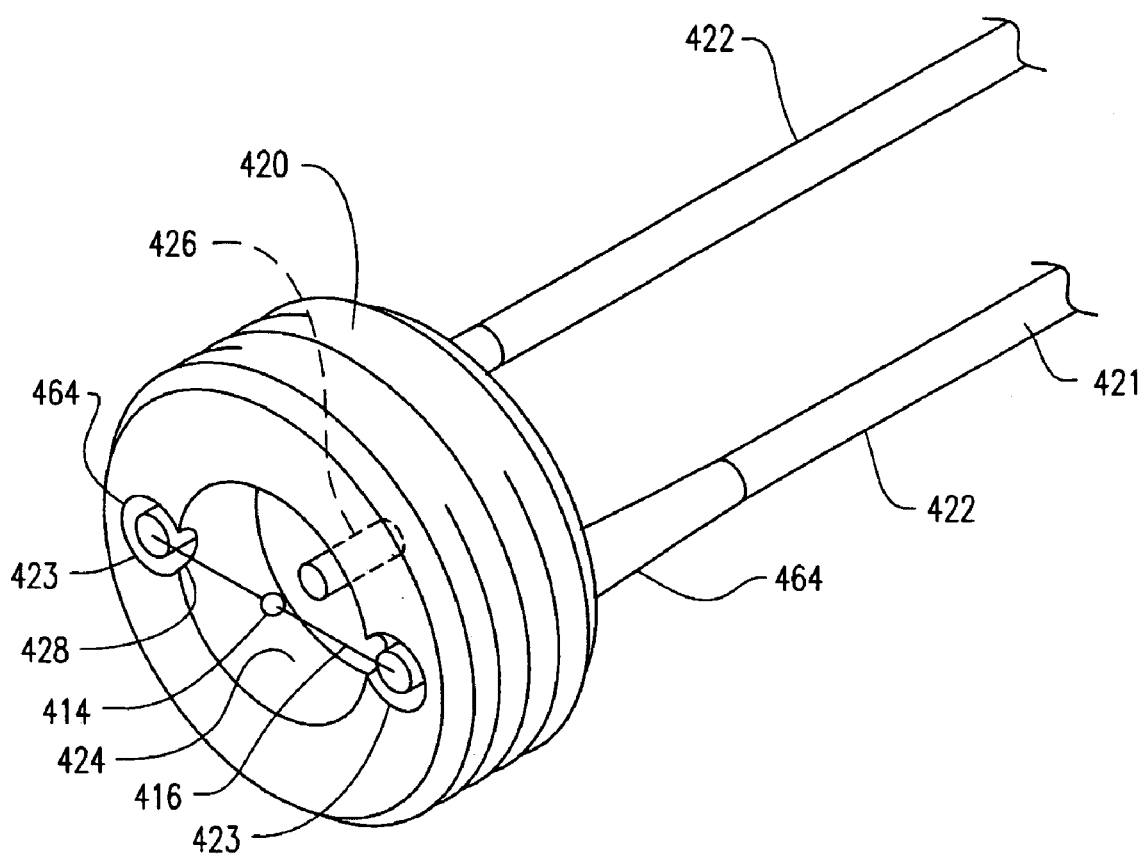

FIG. 28 shows an embodiment of a sensor housing 420 partially assembled with contact pins 422 and a thermistor 414. The sensor housing 420 is desirably made from stainless steel or any other suitable non-reactive material capable of withstanding temperatures over 100° C. The sensor housing 420 comprises an internal cavity 424 that forms at least a portion of the gas analysis chamber. The sensor housing 420 further comprises a bore 423 for each contact pin 422. In some embodiments, each bore 423 runs parallel to the fluid outlet passageway 426. In some embodiment, a portion of each bore 423 overlaps the internal cavity 424, or alternatively, a channel 428 is formed between each bore 423 and the internal cavity 424 so that the thermistor leads 416 do not contact the sensor housing 420.

Each contact pin 422 is insulated from the sensor housing 420, for example using an insulating sleeve 464 comprising polytetrafluoroethylene (PTFE) or any other suitable insulating material. In some embodiments, the insulating sleeves 464 are suitable to both thermally and electrically insulate the contact pins 422 from the sensor housing 420. The contact pins 422 and insulating sleeves 464 are secured to the sensor housing 420 using any suitable method. In some embodiments, the contact pins 422 and insulating sleeves 464 are friction fit within their respective bores 423. In some embodiments, the contact pins 422 and insulating sleeves 464 are bonded to the sensor housing 420 using a curable composition that will resist chemical degradation, such as an epoxy.

In some embodiments, the thermistor 414 comprises a commercially available microthermistor such as a Bead Microthermistor available from YSI Temperature of Dayton, Ohio. In some embodiments, the thermistor 414 is coated in glass and comprises two electrical leads 416. The leads 416 may comprise platinum-iridium, platinum, gold, copper and/or other suitable conductive materials or alloys thereof.

The thermistor 414 is centered between the contact pins 422 and aligned along the longitudinal axis of the fluid outlet passageway 426. Thus, the thermistor 414 is oriented directly in the flow path of the gas stream. Each electrical lead 416 is electrically connected to a contact pin 422, for example by soldering. In some embodiments, the electrical leads 416 and the connections between the leads 416 and the contact pins 422 are coated with a curable composition such as an epoxy. Such a coating provides a further mechanical connection between the leads 416 and the contact pins 422, provides support to the leads 416 against strain and vibration, and also provides a chemical barrier between the flowing gas stream and potentially reactive material(s) used to form the leads 416 and the contact pins 422.

Passing the contact pins 422 through the sensor housing 420 and having the contact pins 422 mechanically supported by the sensor housing 420 prevents external loading and vibrations present in the distal portions 421 of the contact pins 422 from damaging the thermistor 414 or the thermistor leads 416. Thus, the sensor housing 420 allows the thermal conductivity detector 410 to be rugged and useable in field applications.

Referring again to FIG. 27, the body housing 430 comprises an internal cavity 434 that receives the sensor housing 420. The body housing 430 is desirably made from the same material as the sensor housing 420 or any other suitable and compatible material. In some embodiments, the inner surface 435 of the internal cavity 434 and the outer surface 433 of the sensor housing 420 comprise complimentary threadings.

Figure 29:
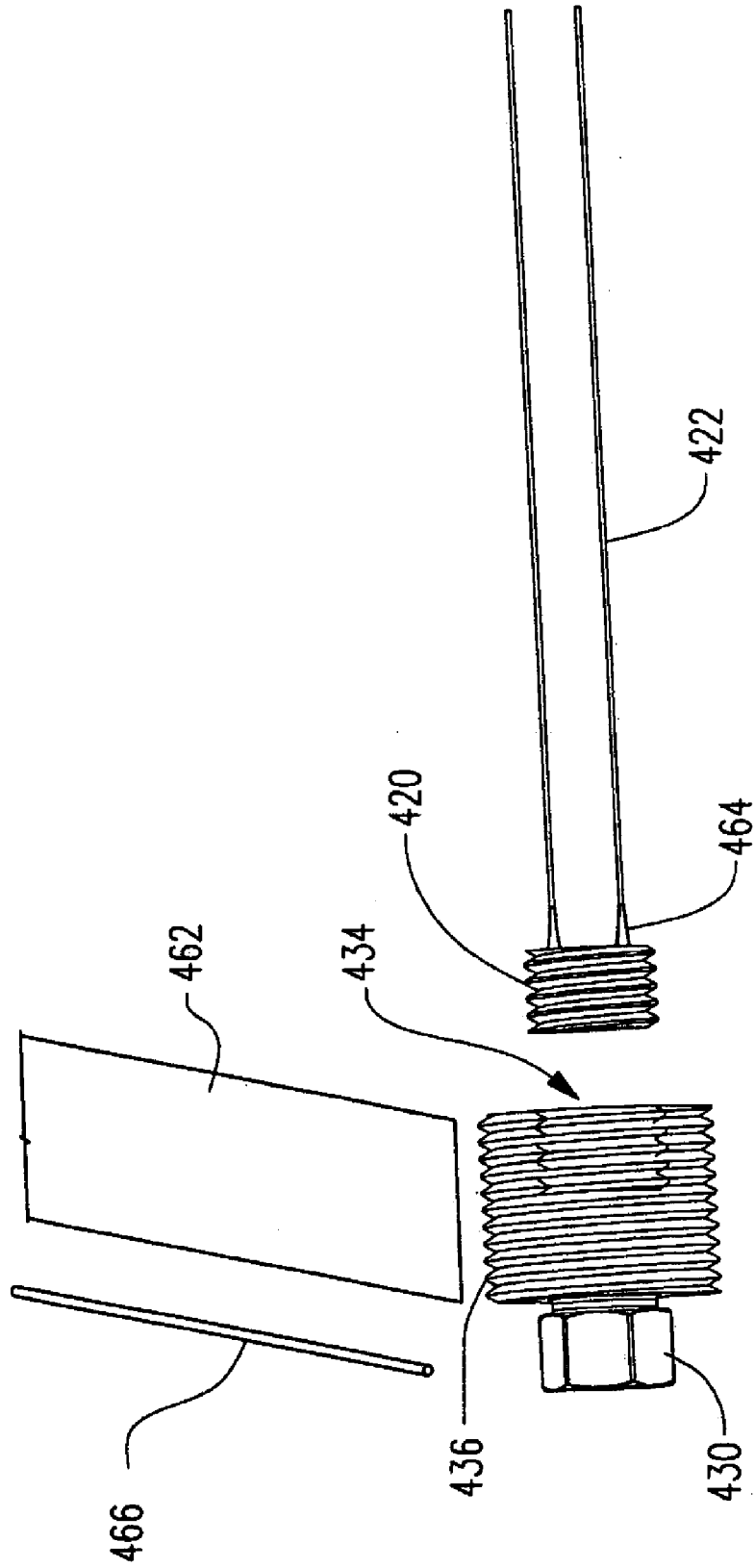

FIG. 29 shows a sensor housing 420 assembled with the contact pins 422 visible and the body housing 430 oriented to receive the sensor housing 420. The sensor housing 420 is inserted/threaded into the internal cavity 434 of the body housing 430, thereby sealing the thermistor 414 within the gas analysis chamber formed by the internal cavities 424, 434 of the sensor housing 420 and the body housing 430. In some embodiments, the sensor housing 420 is further secured to the body housing 430 using a curable composition such as an epoxy. The use of a curable composition further ensures that the gas analysis chamber is hermetically sealed against all air flow except the gas flow being analyzed.

An electrical insulator 462 of any suitable material is oriented about the body housing 430. In some embodiments an insulator 462 comprises PTFE, such as 3 mil PTFE tape that is wrapped about the body housing 430 at least one time and in some embodiments four or more times. In some embodiments, the body housing 430 comprises external threadings 436, and the insulator 462 is desirably thin and flexible enough to conform to the root radius of the threadings 436.

A heating device 466 is then oriented about the insulated body housing 430. In some embodiments, the heating device 466 comprises a resistive heating wire comprising Nickel Chromium or other suitable metals and/or alloys. When the heating device 466 comprises a wire, it is desirably wrapped into the root radius of the external threadings 436 of the body housing 430, and thus comprises a suitable size, such as 30 AWG. A second layer of electrical insulator 462 is then oriented about the body housing 430 to further insulate the heating device 466.

Figure 30:
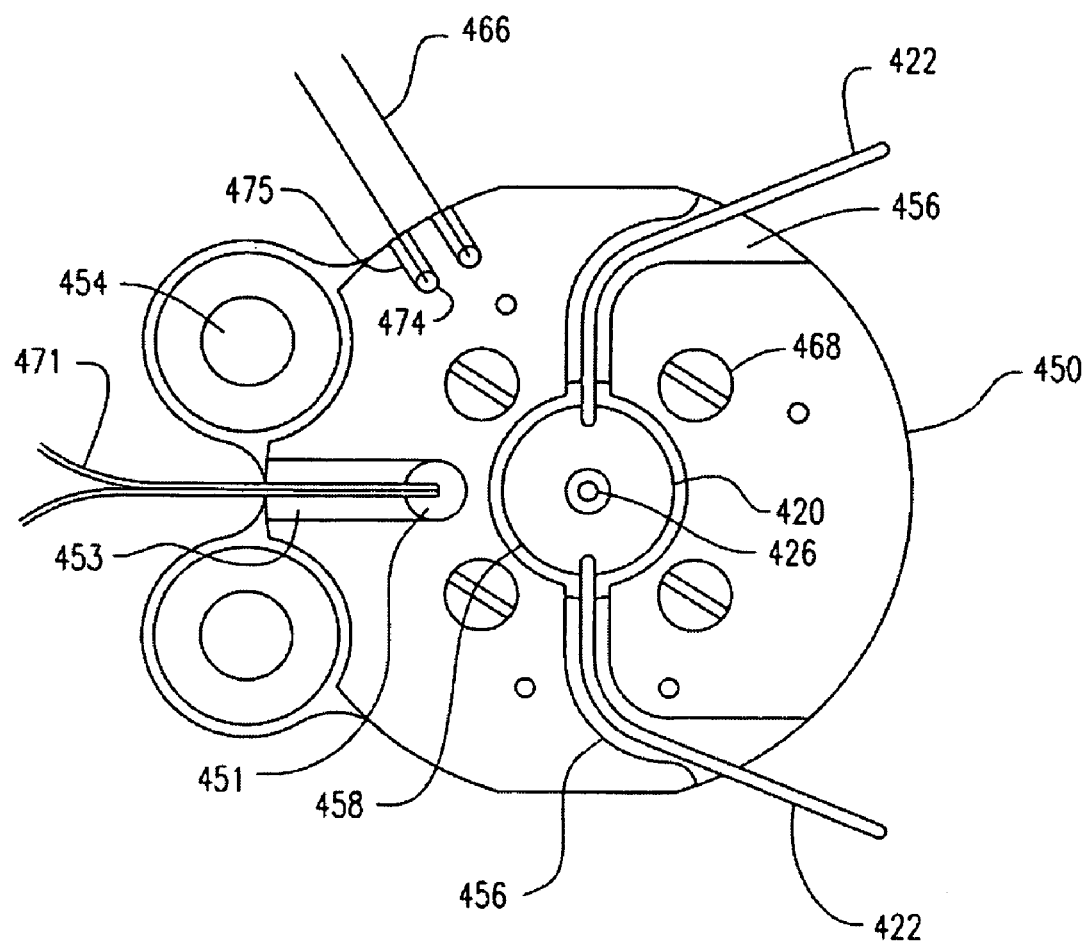
FIG. 30 shows an embodiment of an end plate and other components of a thermal conductivity detector.

Referring to FIGS. 27 and 30, the second end plate 450 comprises an insulative material capable of withstanding temperatures of 100° C. or greater. The material is further capable of being formed or machined to the specific shapes required. In some embodiments, the second end plate comprises G10 epoxy impregnated laminate, for example as available from American Micro Industries, Inc. of Chambersburg, Pa.

The second end plate 450 comprises a plurality of securement apertures 452 (see FIG. 27). A plurality of fasteners 468 pass through the securement apertures and are received in securement cavities 438 in the body housing 430. The second end plate 450 further comprises a channel 456 for each contact pin 422 and a central aperture 458. Each contact pin 422 passes from the sensor housing 420 through the central aperture 458, and is then oriented within its respective channel 456. The contact pins 422 are then electrically connected to the analog signal processing section 32 (see FIG. 9) of the gas chromatograph 5 control system.

In some embodiments, a flow tube 460 is placed in fluid communication with the fluid outlet passageway 426 of the sensor housing 420. The flow tube 460 passes through the central aperture 458 of the second end plate 450 and directs the flow of the gas stream exiting the thermal conductivity detector 410. In some embodiments, the flow tube 460 comprises stainless steel and is bonded to the sensor housing 420 using a curable composition.

In some embodiments, body housing 430 further comprises a temperature sensor cavity 431, and the second end plate 450 further comprises a temperature sensor aperture 451 and a sensor channel 453. Thus, a temperature sensor 470 is placed within the temperature sensor cavity 431 and the associated wiring 471 passes through the temperature sensor aperture 451 and is oriented within the sensor channel 453. The temperature sensor 470 detects the temperature of the thermal conductivity detector 410 and reports the temperature to the analog systems section 66 of the gas chromatograph 5 control system (see FIG. 9).

Referring to FIG. 30, in some embodiments the second end plate 450 further comprises heating wire apertures 474 and heating wire channels 475. The ends of a heating wire 466 that is wrapped about the body housing 430 extend through the heating wire apertures 474 and are oriented within the heating wire channels 475. The ends of the heating wire 466 are then electrically connected to the analog systems section 66 of the gas chromatograph 5 control system (see FIG. 9). The analog systems section 66 controls the temperature of the thermal conductivity detector 410 by increasing and/or decreasing the current flowing through the heating wire 466. The analog systems section 66 adjusts the current in the heating wire 466 based upon the temperature of the thermal conductivity detector 410 as reported by the temperature sensor 470.

The second end plate 450 further comprises at least one mounting aperture 454 used to secure the thermal conductivity detector 410 to the rest of the device. For example, in some embodiments the thermal conductivity detector 410 is received in opening 114 in the GCCA 102 (see FIG. 18), and fasteners pass through the mounting apertures 454 and into a portion of the GCCA housing.

Figure 31:
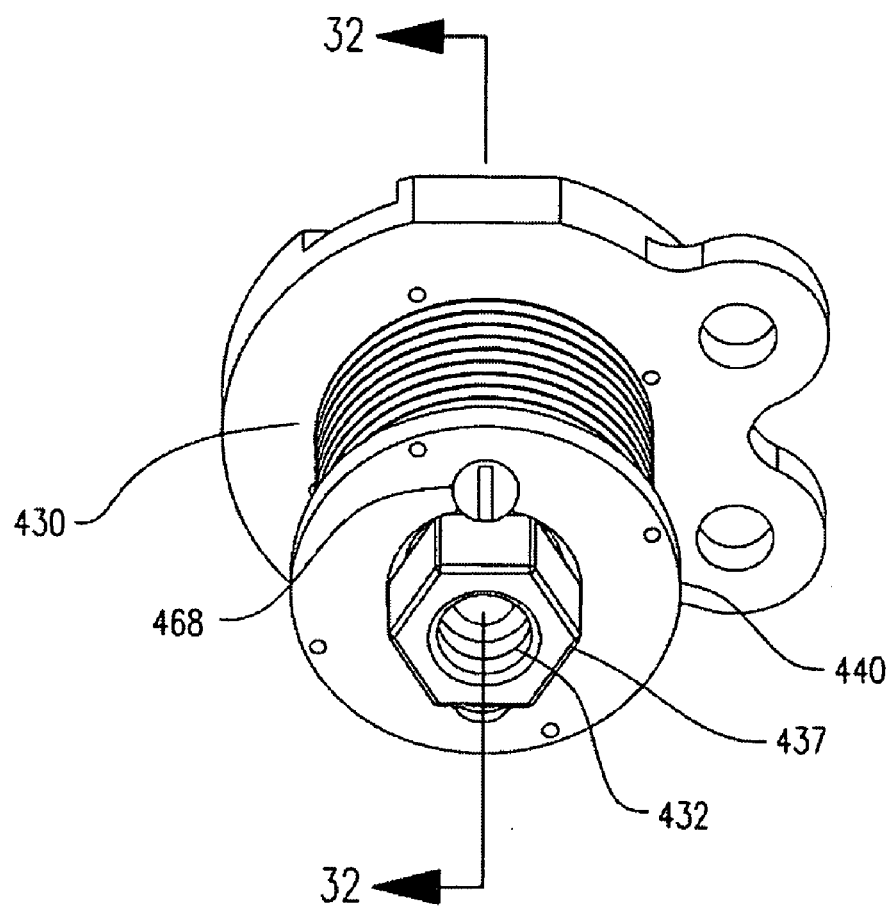
FIG. 31 shows an embodiment of an assembled thermal conductivity detector.

FIG. 31 shows the first end plate 440 secured to the body housing 430 using fasteners 468. The first end plate 440 is desirably made from the same material as the second end plate 450 or another suitable insulative material.

In some embodiments, the body housing 430 further comprises a fitting 437 in conjunction with the fluid inlet passageway 432. The fitting 437 may be used to attach the thermal conductivity detector 410 to the column tubing 144 from the GCCA 102 (see FIG. 22) to receive the gas stream. In some embodiments, the fitting 437 comprises internal threadings.

Referring again to FIG. 27, in some embodiments, the first end plate 440 comprises an aperture 442 shaped to receive the fasteners 468 and the fitting 437.

In some embodiments, the first end plate 440 and the second end plate 450 may each comprise a plurality of alignment pin apertures 448 or blind holes. Alignment pins 446 are then used to aid in assembly and alignment of the end plates 440, 450.

Figure 32:
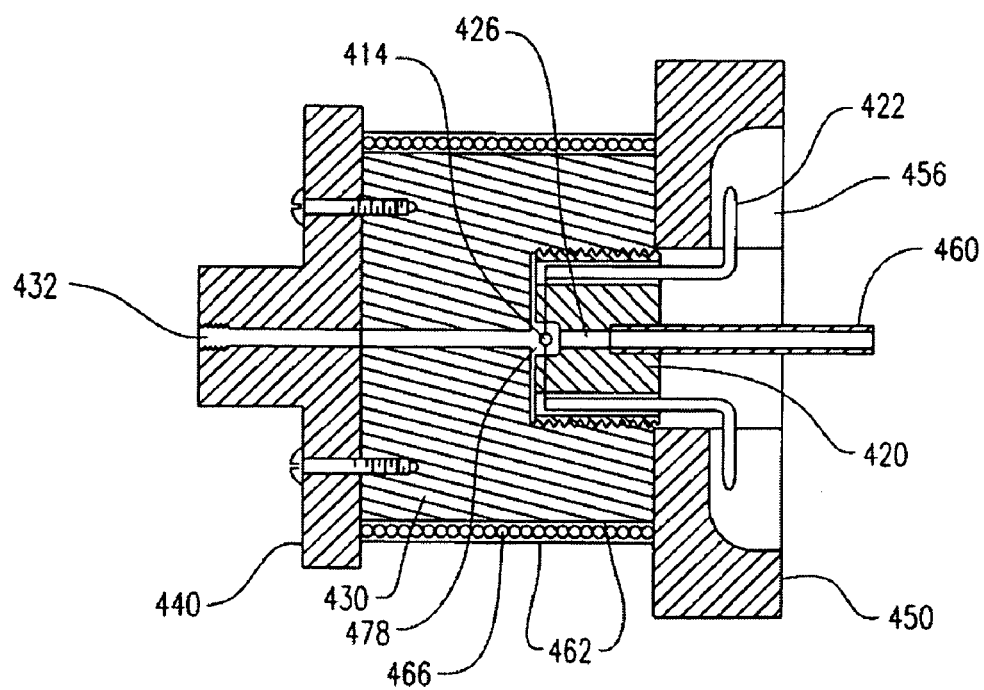
FIG. 32 shows a sectional view of an embodiment of a thermal conductivity detector, for example as taken across line 32-32 of FIG. 31.

FIG. 32 shows a sectional view of an embodiment of a thermal conductivity detector 410, for example as taken across line 32-32 of FIG. 31. The gas analysis chamber 478, formed by the internal cavities of the sensor housing 420 and the body housing 430, is visible with the thermistor 414 suspended therein. Similar reference numerals are used to denote similar features as shown and described with respect to FIGS. 27-31.

Very Small High Pressure Regulator (VSHPR)

Figure 33:
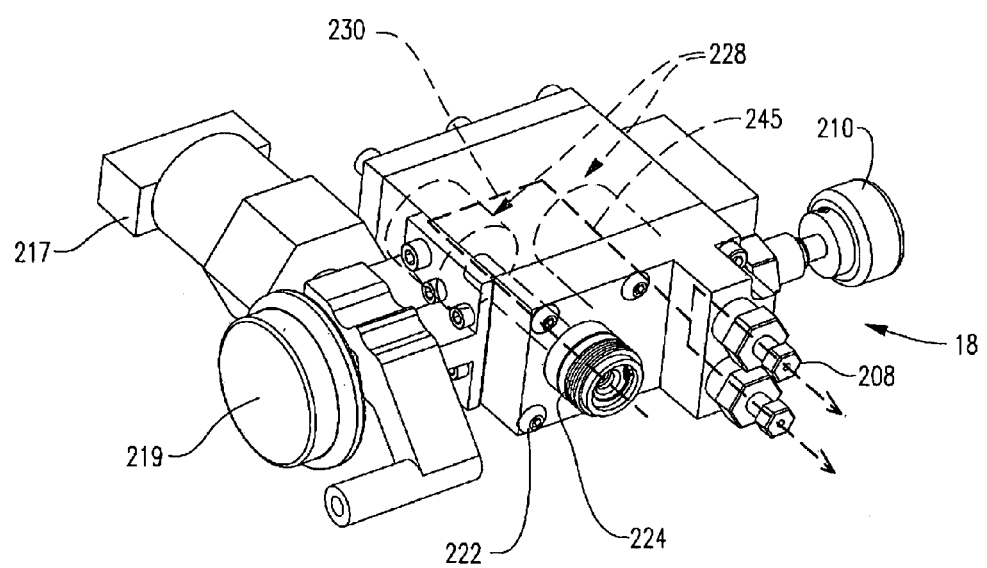
FIG. 33 is a partially transparent perspective view of a Very Small High Pressure Regulator.

Referring now to FIG. 33, there is shown a partially transparent view of the Very Small High Pressure Regulator (VSHPR) (18). In at least one embodiment, the VSHPR (18) is a component of a Gas Chromatograph. In at least one embodiment, the VSHPR (18) is a stand alone device not connected to a Gas Chromatograph. The VSHPR (18) regulates the flow and pressure of a gas stream which enters from a source (not shown) and subsequently exits out of one or more outlets (208) positioned at the opposite end of a gas flow path (245). The gas flow path (245) of the VSHPR (18) comprises two or more gas stages (228) which work together to reduce the pressure of received input gas from as high as 3000 psi to a constant output pressure which can be as low as 30 psi. In at least one embodiment, the VSHPR (18) is calibrated for any input or output pressure within the 3000–30 psi range and is accurate with a precision of +/−1psi. In at least one embodiment, the VSHPR (18) has small compact dimensions and is designed to fit in any portable or hand held equipment that uses high pressure gas. In at least one embodiment, the VSHPR has dimensions of 1.25"×2.75"×4.64".

In at least one embodiment, the VSHPR reduces the pressure from 2000 psi to 40 psi. 2000 psi is a common pressure level in gas sources such as commercially available gas tanks or bottles and in particular of helium gas bottles. The regulation to a constant and stable pressure of 40 psi allows the gas stream to be properly used by other components of the Gas Chromatograph. The VSHPR (18) can regulate a gas stream consisting of a gas selected from the list of helium, hydrogen, any other gas with a molecular mass greater than helium, and any combination thereof. In at least one embodiment the VSHPR (18) comprises one or more O-Rings and/or one or more lubricants (including but not limited to polysiloxane) and/or one or more sealants to assure that the gas being input into the VSHPR (18) does not leak or become contaminated.

The gas stream enters the VSHPR (18) from a gas source by passing through an inlet port (224). The inlet port (224) can be of any shape or configuration known in the art but in at least one embodiment it is an industry standard C-10 inlet subassembly. The C-10 inlet subassembly has a specific diameter and comprises a flange (not shown) which impacts against and pushes open the gas source (such as a C-10 adapted gas bottle) once it is attached to the C-10 inlet subassembly. As a result, attaching the gas source to the C-10 inlet assembly places the gas source in fluidic communication with the VSHPR (18). In at least one embodiment the inlet port (224) is engaged to a third O-Ring (204) (see FIG. 35) to assure an air tight seal exists between the gas source and the inlet port (224).

The gas flow path (245) of the VSHPR (18) utilizes at least two regulator stages (228) in fluidic communication with each other, one being a first stage (228') and a second being a second stage (228"). Each of the regulator stages (228) reduces the pressure of the gas stream from a provided level to a reduced level.

In at least one embodiment, the first stage (228') performs a gross pressure reduction reducing the provided input pressure to an intermediate pressure. In at least one embodiment the input pressure is quantified in terms of thousands of psi (3000-1000 psi) and the intermediate pressure is quantified in terms of hundreds of psi (999.999-100 psi). The second stage (228") performs a fine pressure reduction reducing the intermediate pressure to a desired output pressure. In at least one embodiment the intermediate pressure is quantified in terms of hundreds of psi (999.999-100 psi) and the output pressure is quantified in terms of tens of psi (99.99 psi-30 psi). In at least one embodiment, the first stage reduces the pressure from an input pressure of approximately 2000 psi to an intermediate pressure of approximately 200 psi. In at least one embodiment, the second stage reduces the pressure from an intermediate pressure of approximately 200 psi to an output pressure of approximately 40 psi. In at least one embodiment, the VSHPR comprises stages (228) which lie parallel to each other. By placing the stages (228) in an oppositely directed parallel configuration, a more compact design than found in prior art gas regulator can be realized.

In FIG. 33, the inlet port (224) and the gas output port(s) (228) are located at or near one side of the VSHPR (18) and the conduit (230) which transfers gas between the first stage (228') and the second stage (228") is located at or near the opposite side of the VSHPR (18). For purposes of this application, the term "inlet side" refers to the side of the VSHPR where the inlet port (224) is located and the opposite side of the VSHPR is referred to as the "transfer side". Similarly any given item can be said to have its transfer side and its inlet side. The transfer conduit (230) need not necessarily be on the VSHPR's transfer side and at least one embodiment has the transfer conduit (230) positioned anywhere in or along the VSHPR (18). Similarly the gas output(s) (228) need not necessarily be on the inlet side of the VSHPR (18) at least one embodiment has it positioned along any external region of the VSHPR (18).

In at least one embodiment, the VSHPR (18) comprises one or more diagnostic devices (231). Diagnostic devices (231) include but are not limited to a pressure gauge (219) and/or an electrical pressure switch (217). The pressure gauge (219) refers to any mechanical and or electrical device known in the art that provides a visible display of the pressure within a particular location of the VSHPR (18). The pressure switch (217) monitors the gas pressure and is capable of electronically relaying diagnostic information to any other component of the Gas Chromatograph or any other device. In at least one embodiment the diagnostic device (231) is in fluidic communication with the junction (232) connecting gas inlet (224) and the first stage (228'). When the pressure at this junction (232) drops below a particular pre-determined level (which in at least one embodiment is <=300 psi) as a result of the supply in the gas source being either depleted or close to depletion, a new source should be procured and supplied to the VSHPR (18). In at least one embodiment the pressure switch (217) is integrated into an online inventory and maintenance system capable of monitoring the gas supply, determining and indicating when new gas sources need to be installed, and appropriately ordering gas sources from vendors or suppliers to assure sufficient inventory is always on hand. In at least one embodiment, at least one diagnostic device (231) is connected to at least one other component of the VSHPR (18) by a regulator mount (218).

Figure 42:
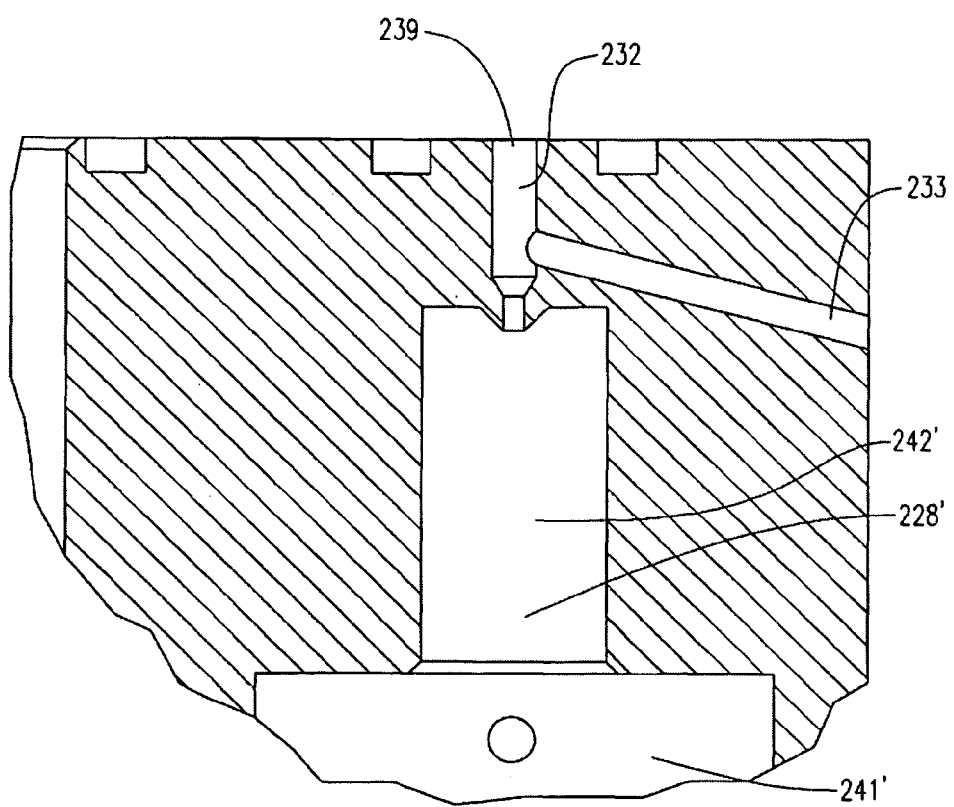
FIG. 42 is an overhead cut-away view of a portion of the center block.

FIG. 42 illustrates a junction (232) between the gas inlet (224) and the first stage (228'). Extending away from junction (232) is a diagnostic conduit (233). The diagnostic conduit (233) is in fluidic communication with the junction (232), the inlet port (224) and the gas source. When the gas source runs low the pressure in the diagnostic conduit (233) drops below a particular value which is detected by the one or more diagnostic devices (231) in fluidic communication with the diagnostic conduit (233). In at least one embodiment, one or more similar diagnostic conduit can connect similar or other diagnostic devices (231) to other parts of the VSHPR (18) including but not limited to diagnostic conduits extending into the gas conduit (230) or any region downstream from the second stage (228").

Figure 34:
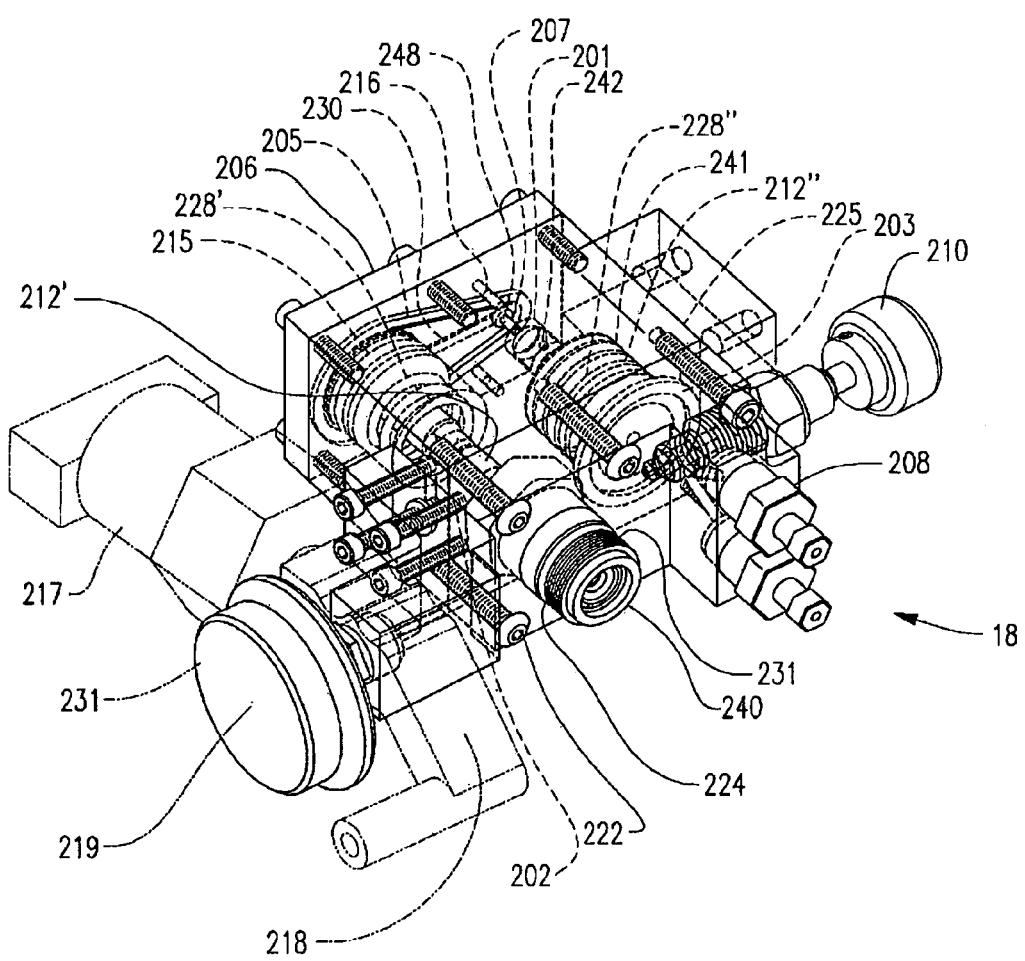
FIG. 34 is a highly transparent perspective view of a Very Small High Pressure Regulator.

Referring now to FIG. 34 there is shown a more transparent view of the VSHPR (18). The first stage (228') comprises a first piston (212') biased to move in one direction. The bias can be achieved by a first biasing mechanism (201') such as a spring or other mechanism known in the art. When gas first enters the first stage (228') it builds up a countervailing force which is applied according to a vector opposite to the force exerted by the first biasing member (201'). Eventually the countervailing gas pressure force exceeds that of the biasing force causing the first piston (212') to be moved and to sever the fluidic communication between the first junction (232) and the first stage (228'). The contained gas is then bled off into the gas conduit (230) connecting the first stage (228') and the second stage (228"). The bleeding reduces the gas pressure of the gas stream from the input pressure level to the intermediate pressure level.

The second stage (228") operates in a similar manner to the first stage but has its second piston (212") in an orientation opposite to that of the first stage (228'). As the gas stream flows into the second stage (228") from the gas conduit (230) pressure builds up in the second stage (228"). When the gas pressure reaches a predetermined level (equal to the output pressure level) the gas exerts a countervailing force which overcomes the biasing force of the second biasing members (201"). This pushes the second piston (212") to sever the fluidic communication between the gas conduit (230) and the second stage (228"). The movement also allows the gas to exit the second stage (228"), enter the second junction (238) at the reduced output pressure, and flow towards the gas output (228). Although FIG. 42 illustrates the two stages (228) extending along substantially parallel axis, in at least one embodiment they are oriented in any configuration relative to each other.

In at least one embodiment, there are multiple stages each having an entering gas pressure and an exiting gas pressure. The exiting gas pressure of an upstream stage provides the entering gas pressure of the immediately downstream stage. The stages have pistons (212) with narrow shafts and wide compression rings (243). The compression rings block gas flow by moving into a closed configuration blocking the engagement point between the narrow and wider chambers of the stage when the entering pressure in the narrow chamber exceeds an activation level which is too high. The compression rings move away from the narrow chamber and assumes an open configuration when gas downstream from the compression ring drops to the appropriate level allowing more gas to move downstream at an exiting pressure which is a reduced pressure level.

In at least one embodiment the second junction (238) comprises a closing mechanism (210) such as a valve. The closing mechanism (210) allows for the VSHPR (18) to dynamically alter the flow of the gas stream while using a constant flow gas source such as a commercially available C-10 adapted gas bottle. The closing mechanism (210) can be a manually rotating device or knob, can be a switch, or can be an electronic device which receives input and provides output to a controller device or computer. In at least one embodiment, the closing mechanism (210) dynamically interacts with data sent and received between itself and a pressure switch. In at least one embodiment this interaction causes the closing mechanism to shut off gas flow when the pressure from the gas source drops below a particular value or in response to any other user defined reason or data input. The closing mechanism (210) can be binary (allowing for only an open or closed setting), can shunt gas flow between one, some, or all of the one or more gas outlets (208), or can be used to modulate the amount of gas that passes through the outlet(s) (208).

Figure 35:
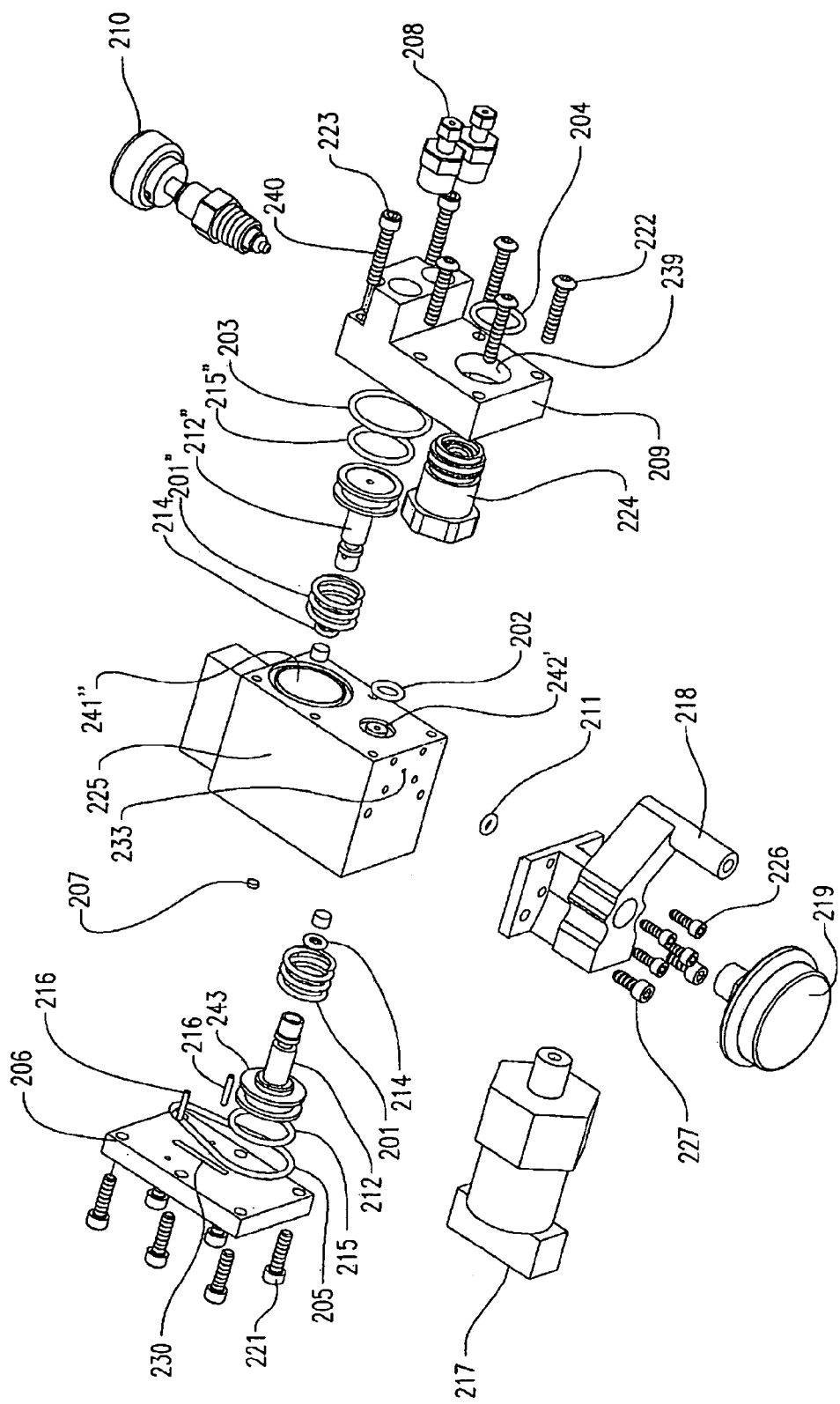
FIG. 35 is an exploded perspective view of a Very Small High Pressure Regulator.

Referring now to FIG. 35 there is illustrated an exploded view of at least one embodiment in which a VSHPR (18) comprises a number of component parts. In at least one embodiment, at least some of the parts are common commercially available parts which are assembled at least in part according to schematic of FIG. 3. In at least one embodiment, a number of O-Rings (202, 203, 204, 205, 211, 214, and 215) are positioned between components to assure airtight seals form between them. The inlet side of the VSHPR is defined by an inlet plate (209) having three apertures on the inlet side and at least one on the transfer side. One inlet side aperture is the opening to the gas source (239). In at least one embodiment, the gas source opening has an O-ring (204) at its end to better assure a fluid tight seal between the VSHPR (18) and the gas source. Some or all of the inlet port (224) can be defined by a through hole passing through solid material of the inlet plate, or it can be a hollow polygonal mass placed within an at least partially hollow inlet plate (209). Similarly the opening to the outlet (240) can be defined by through holes extending through solid material of the inlet plate (209) or it can be defined by a hollow polygonal mass placed within an at least partially hollow inlet plate (209). The outlet opening (240) has one aperture at the transfer side in fluidic communication with the second stage (228") and can have one, two or more branches extending out of apertures at the inlet side of the inlet plate (209) to of tube adaptors (208). In at least one embodiment a two branch outlet port adaptor (208) extends through the inlet plate (209) and out of the outlet opening (240) for engagement to other portions of the Gas Chromatograph or to another device.

In at least one embodiment, between and engaged to both the inlet plate (209) and the transfer plate (206) is a center block (225). In at least one embodiment, the center block defines the walls of the stages (228). In at least one embodiment, the center block (225) is at least partially hollow and contains a shaped polygonal mass of the stage walls. The two or more stages (228) comprise a wide chamber (241) and a narrow chamber (242) in fluid communication with each other. The first stage (228') has the narrow chamber (242') engaged to either the first junction (232) or to the source opening (224). In at least one embodiment between the first stage narrow chamber and the either first junction (232) or to the source opening (224) is an O-ring.

In at least one embodiment the second stage (228") comprises a wide chamber (241") adjacent to the outlet opening (240) and a narrow chamber (242") adjacent to the gas conduit (230). In all of the stages (228) the piston (212) comprises at least two portions a wider piston portion (243) and a narrow piston portion (244). The wide portion (243) fits within the wide chamber (241) and the narrow portion (244) fits within the narrow chamber (242). Each of the pistons (212) are capable of synchronous motions assuring that three different pressure differential equilibriums (the input pressure, the intermediate pressure, and the output pressure) are reached throughout the VSHPR and that the gas stream flows out of the gas flow path (245) at a constant and even rate. In at least one embodiment the wide portion (243) comprises two solid masses with an O-ring positioned at least partially between the two solid masses to assure a fluidic seal within the piston (212). The inventive concept also contemplates all other piston or piston-like equivalents known in the art.

In at least one embodiment, the gas conduit (230) connecting the two stages (228) is defined by hollow volume within the transfer plate (206). The hollow volume can itself be defined by a hollow in the solid mass of the transfer plate (206) or the transfer plate (206) can itself be somewhat hollow with a solid conduit extending through at least a portion of the somewhat hollow transfer plate (206). In at least one embodiment the stage end at the transfer side of the two or more stages (228) are bound by a common O-Ring (205). This common O-Ring (205) can further define an open volume in fluidic communication with the gas conduit (230).

In at least one embodiment, between the second stage (228") and the gas conduit (230) is a frit (207). The frit can also be bound by the common O-ring (205). The frit can be an assembly comprising fibers or granules which filters out unwanted materials. In at least one embodiment a frit (207) capable of filtering out materials with a size >=10 microns is positioned adjacent to the second stage (228"). In at least one embodiment, one or more frits are similarly positioned elsewhere in the VSHPR downstream from the gas source.

In at least one embodiment, the center block (225) is connected to either or both of the transfer plate (206) and the inlet plate (209) by screws (222, 223, 226, and 227). In at least one embodiment, some or all of the three are integrated pieces of material. Similarly in at least one embodiment, the diagnostic devices (231) are connected to the center block (225) by a mount regulator (18) which is welded or bolted to the center block (225) or together define a single integrated piece of material.

Figure 36:
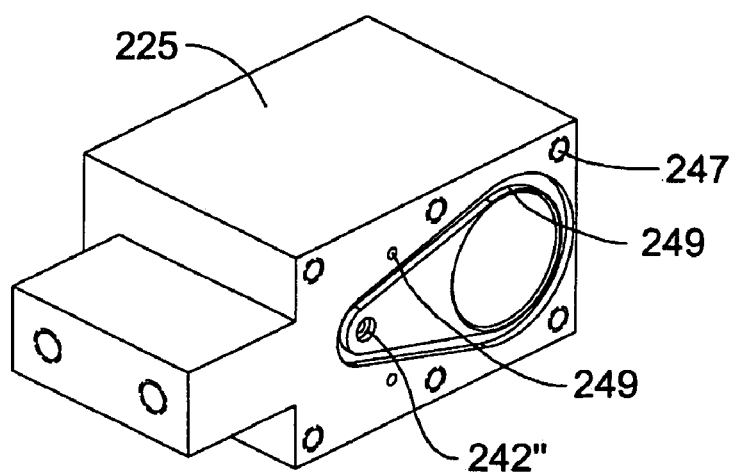
FIG. 36 is perspective view of a center block seen from the inlet side.
Figure 37:
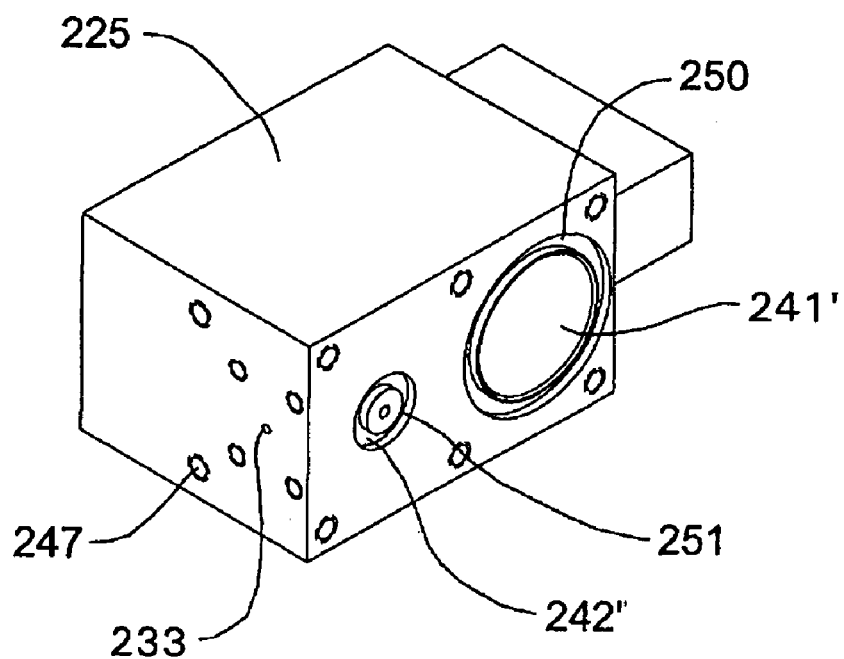
FIG. 37 is perspective view of a center block seen from the transfer side.

FIGS. 36 and 37 illustrate perspective views of the center block (225). FIG. 36 illustrates the transfer side of the center block where the first stage large chamber (241') abuts the transfer plate. Similarly a smaller opening (242") engaged to the second stage (228") lies on the transfer side of the central block (225). In at least one embodiment, a fit is positioned between the small chamber (242") and the transfer plate. In at least one embodiment, dowel pins (216 in FIGS. 34 and 35) can be inserted in dowel holes (246) in the center block (225) to hold the common O-Ring (205) in place. Screw holes (247) can be used to engage the center block to other portions of the VSHPR (18). In at least one embodiment, a common O-Ring cavity (249) is recessed in the center block (225) to fit the Common O-Ring (205).

Figure 38:
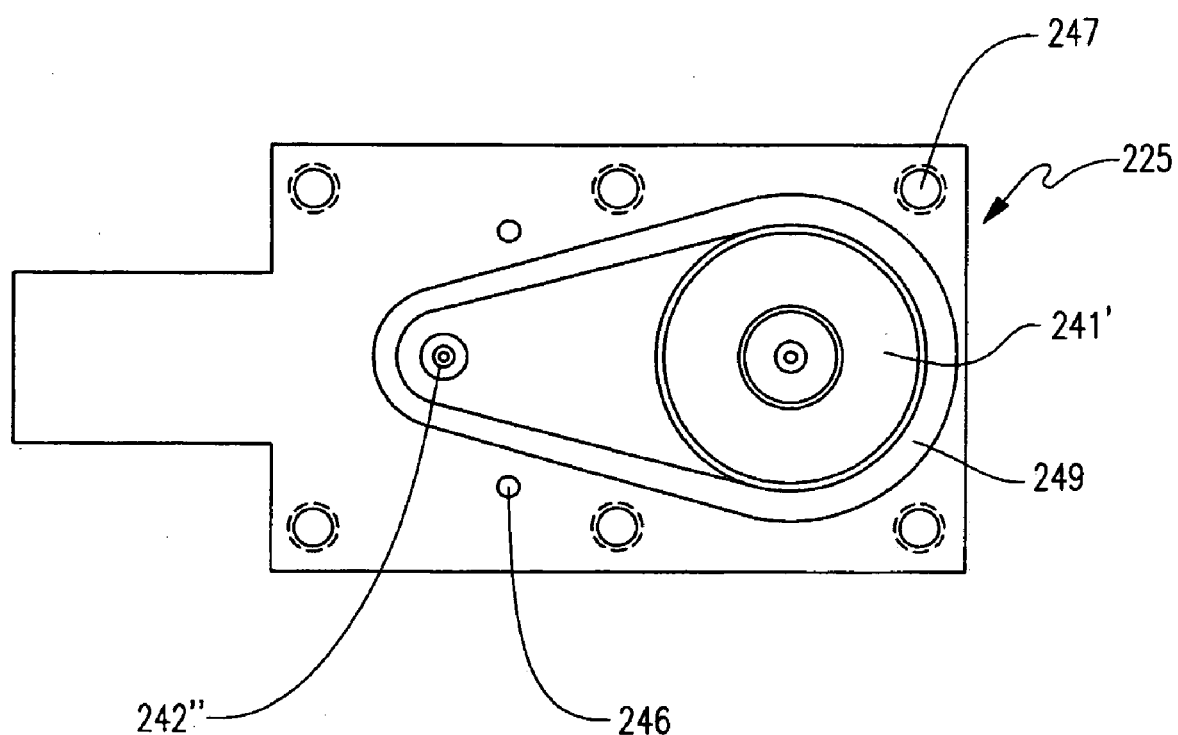
FIG. 38 is lateral view of the center block seen from the transfer side.
Figure 39:
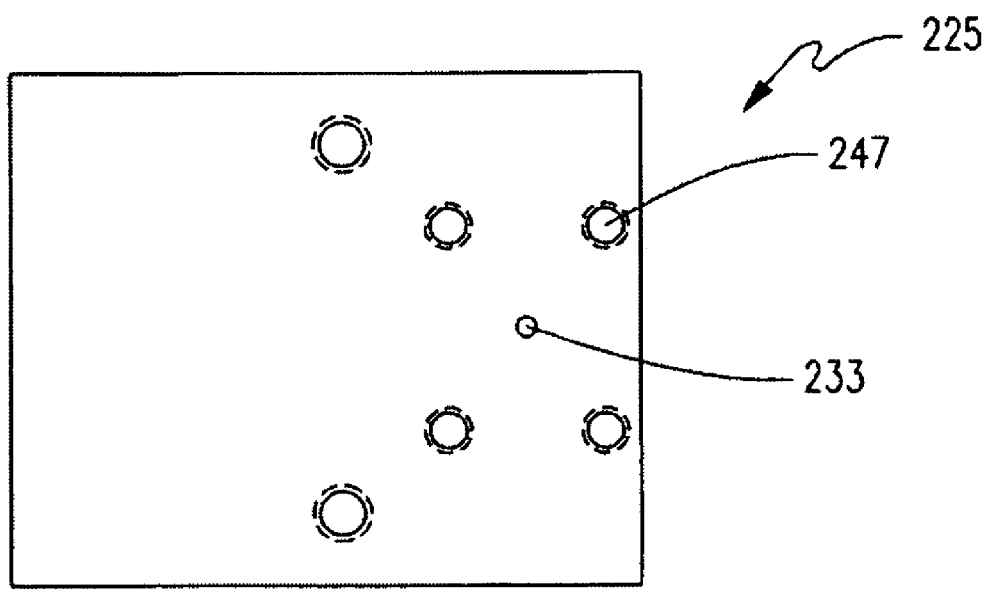
FIG. 39 is lateral side view of the center block.
Figure 40:
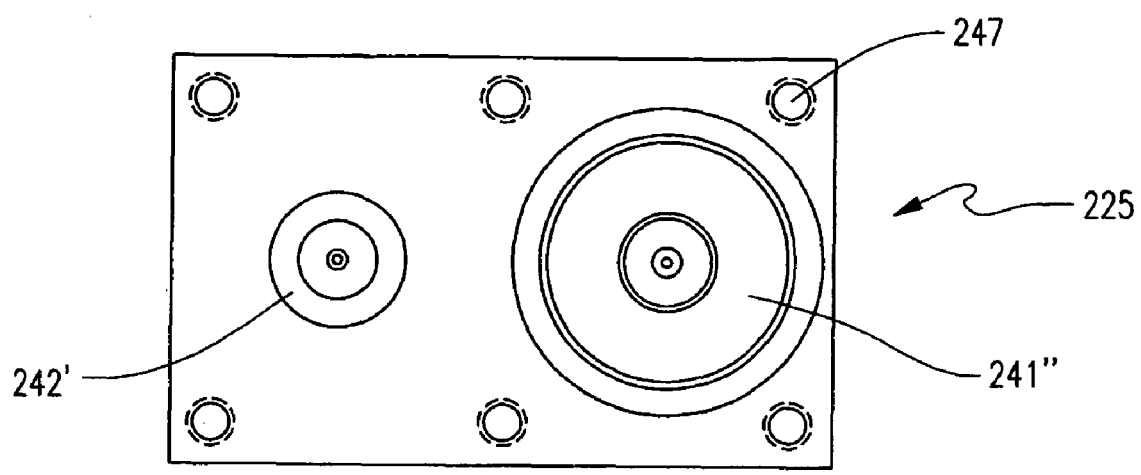
FIG. 40 is lateral view of the center block seen from the inlet side.

FIG. 37 illustrates the inlet side of the center block (225) where the first stage large chamber (241') abuts the inlet plate. Screw holes (247) connect the center block to the inlet plate and to the mount regulator. A diagnostic conduit (233) connects the gas flow path to diagnostic components. The narrow chamber (242') of the first stage gas and the wide chamber (241) of the second stage are also shown. O-Rings (202 and 203 in FIG. 35) are positioned between these chambers and the inlet plate. FIGS. 38-40 show lateral perspective views of the center block (225). FIG. 37 also shows recesses (250 and 251) to hold O-Rings in place.

Figure 41:
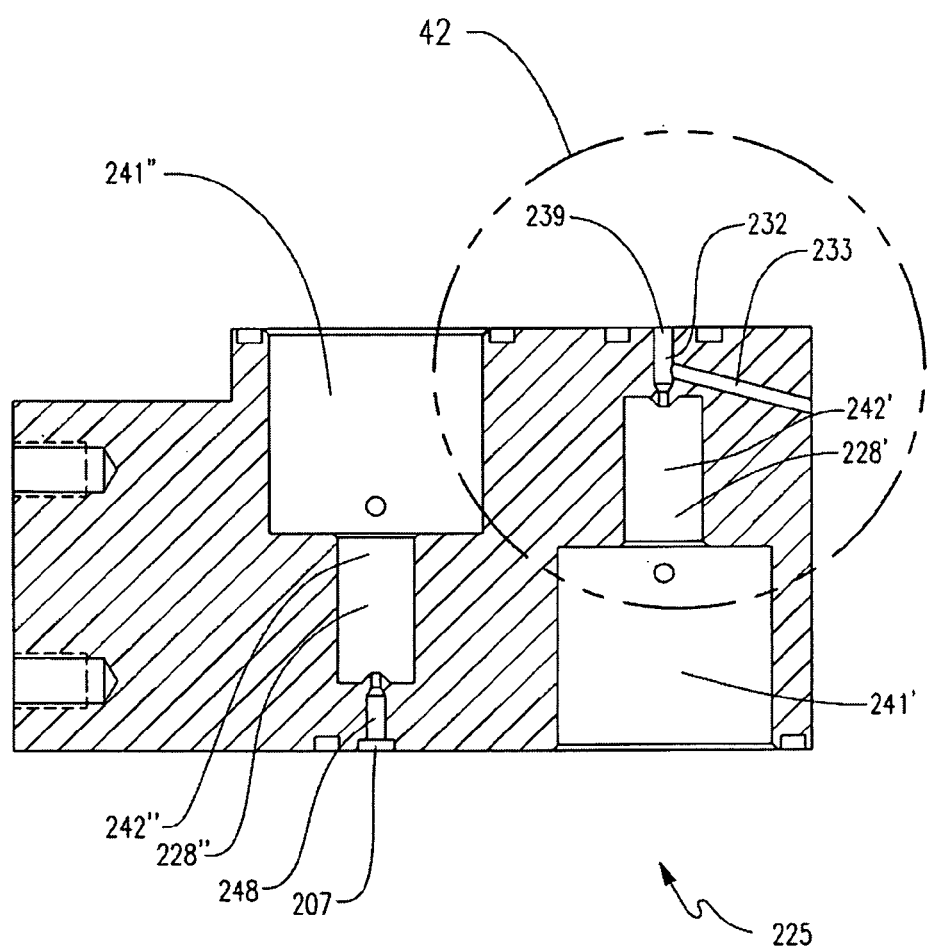
FIG. 41 is an overhead cut-away view of the center block.

FIG. 41 shows a cut away view of at least one embodiment in which the solid mass of the center block (225) defines the walls of the stages (228). The center block (225) also has a diagnostic conduit (233) and a pre-stage conduit (248) connecting the second stage (228") to the transfer plate. A frit (207) is positioned at the transfer side of the pre-stage conduit (248).

Figure 43:
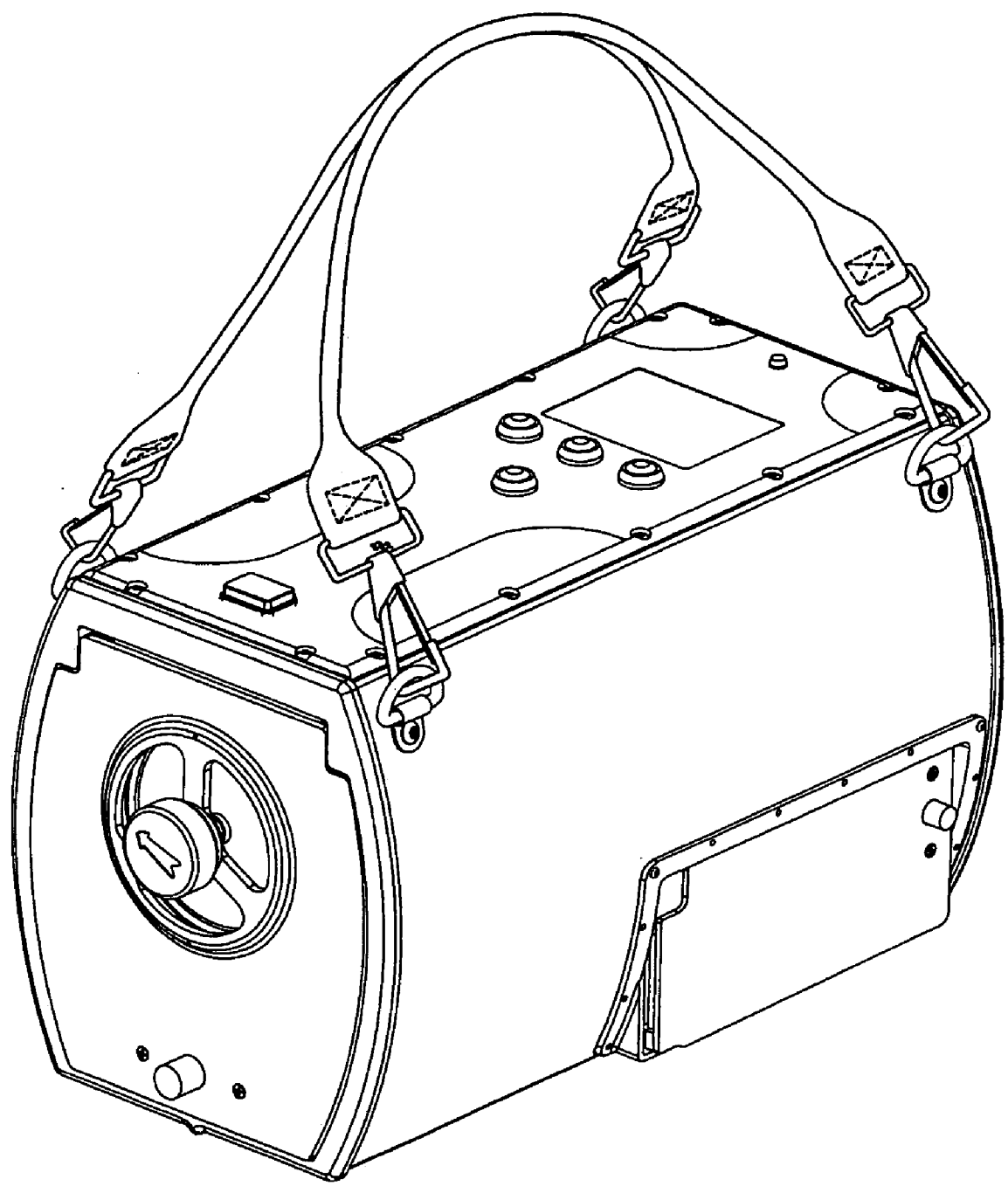
FIG. 43 is a photograph of an embodiment of a portable gas chromatograph according to the invention.

The portable gas chromatograph disclosed and claimed herein, is compact and lightweight. Furthermore, it may include handles for easy transport from location to location. A perspective view of an embodiment of a gas chromatograph according to the invention is shown in FIG. 43.

Figure 44:
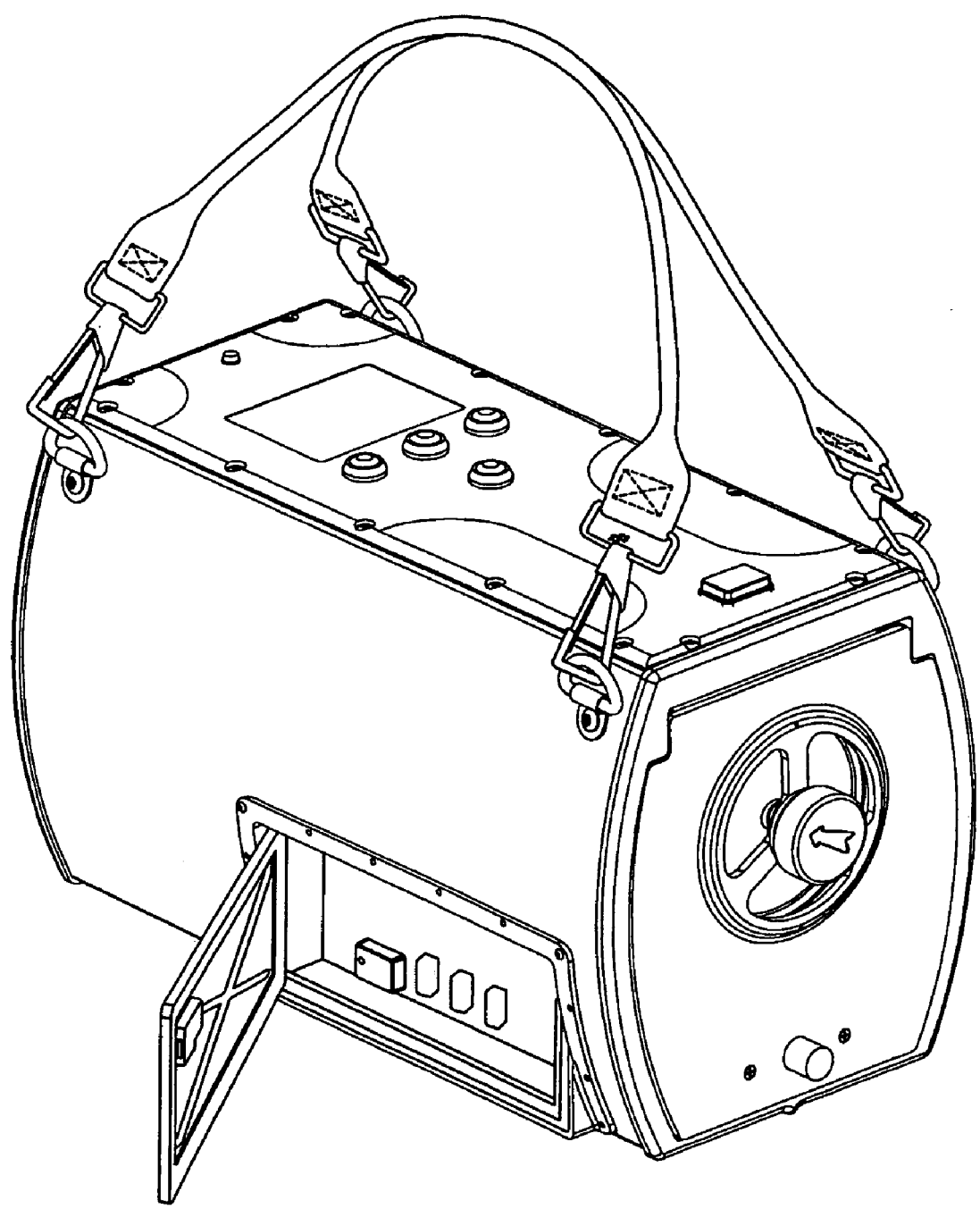
FIG. 44 is a photograph showing a side panel in the system for accessing the regulator shut-off valve.

FIG. 44 shows a side panel which allows access to the regulator 18's shut-off valve.

Thus, the present invention has the capability of analyzing chemicals, particularly those extracted from the surrounding environment, developing a signature for each component/analyte of the sample, store the signature and send it to a computer via a wireless radio system.

Examples of suitable applications include, but are not limited to, portable chemical identification, facility HVAC security, biological agent identifier, and so forth.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims

The invention claimed is:

1. A portable multi-dimensional gas chromatograph, the gas chromatograph comprising:
 a carrier gas container;
 a regulator fluidly connected to the carrier gas container;
 a dopant chamber containing a reference chemical;
 at least one pre-concentrator which is fluidly connected to the regulator and the dopant chamber;
 a separation column fluidly connected to the at least one pre-concentrator;

a thermal conductivity detector fluidly connected to the first separation column;

wherein the thermal conductivity detector comprises:

a housing having an internal gas analysis chamber, a fluid inlet passageway in communication with the gas analysis chamber, a fluid outlet passageway in communication with the gas analysis chamber, and a first bore extending through at least a portion of the housing, the first bore in fluid communication with the gas analysis chamber, the first bore offset from the fluid inlet passageway and the fluid outlet passageway;

a thermistor having an electrical lead; and a first contact pin electrically connected to said electrical lead;

wherein the first contact pin is oriented within the first bore, and the first contact pin is electrically insulated from the housing and mechanically secured to the housing.

2. The portable multi-dimensional gas chromatograph of claim 1, the thermal conductivity detector further comprising a second contact pin, the housing further comprising a second bore in fluid communication with the gas analysis chamber, the thermistor further comprising a second electrical lead electrically connected to the second contact pin, wherein the second contact pin is oriented within the second bore, and the second contact pin is electrically insulated from the housing and mechanically secured to the housing.

* * * * *

UNITED STATES PATENT AND TRADEMARK OFFICE
CERTIFICATE OF CORRECTION

PATENT NO.        : 7,735,352 B2
APPLICATION NO.   : 11/435375
DATED             : June 15, 2010
INVENTOR(S)       : Sheena Alm et al.

It is certified that error appears in the above-identified patent and that said Letters Patent is hereby corrected as shown below:

Column 4, Lines 26-27, delete "FIG. 9A shows more detailed circuit schematics for the block diagram of FIG. 9.";
Column 4, Lines 30-31, delete "FIG. 10A-1 through 10A-29 are more detailed circuit schematics of the various blocks of digital board, of FIG 10.";
Column 4, Lines 34-36, delete "FIG. 11B and FIG. 11C are more detailed circuit schematics showing how the detectors are connected to the FPGA peripheral controller/data formatter.";
Column 4, Line 47, delete "vies" and insert --view--;
Column 22, Line 6, delete "fit" and insert --frit--;
Column 22, Line 56, after the word "claims" insert --.--.

Signed and Sealed this

Twenty-fourth Day of August, 2010

David J. Kappos
*Director of the United States Patent and Trademark Office*